US010060915B2

(12) United States Patent
Fu et al.

(10) Patent No.: US 10,060,915 B2
(45) Date of Patent: *Aug. 28, 2018

(54) MULTIFUNCTIONAL NANOPARTICLES FOR MOLECULAR AND CELLULAR SEPARATION, DETECTION AND QUANTIFICATION

(71) Applicant: NVIGEN, INC., Sunnyvale, CA (US)

(72) Inventors: Aihua Fu, Sunnyvale, CA (US); James Zhu, Cupertino, CA (US)

(73) Assignee: NVIGEN, INC., Sunnyvale, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 14/389,378

(22) PCT Filed: Apr. 1, 2013

(86) PCT No.: PCT/US2013/034866
§ 371 (c)(1),
(2) Date: Sep. 30, 2014

(87) PCT Pub. No.: WO2013/149266
PCT Pub. Date: Oct. 3, 2013

(65) Prior Publication Data
US 2015/0051102 A1 Feb. 19, 2015

Related U.S. Application Data

(60) Provisional application No. 61/618,779, filed on Mar. 31, 2012.

(51) Int. Cl.
*G01N 33/543* (2006.01)
*G01N 21/64* (2006.01)
(Continued)

(52) U.S. Cl.
CPC ......... *G01N 33/54346* (2013.01); *B03C 1/01* (2013.01); *B03C 1/30* (2013.01);
(Continued)

(58) Field of Classification Search
CPC .................................. G01N 33/54346
See application file for complete search history.

(56) References Cited

U.S. PATENT DOCUMENTS 7,501,287 B2 * 3/2009 Orning ............... C07K 16/18
435/7.1
8,722,017 B2 * 5/2014 Fu ...................... A61K 49/0002
424/9.32
(Continued)

FOREIGN PATENT DOCUMENTS

WO  2009-047587 A1  4/2009
WO  2013/123525 A1  8/2013

OTHER PUBLICATIONS

Kim et al., "Multifunctional Uniform Nanoparticles Composed of a Magnetite Nanocrystal Core and a Mesoporous Silica Shell for Magnetic Resonance and Fluorescence Imaging and for Drug Delivery", Angew. Chem. Int. Ed., vol. 47, pp. 8438-8441, published Aug. 25, 2008.*
(Continued)

*Primary Examiner* — Tracy Vivlemore
*Assistant Examiner* — Nam P Nguyen
(74) *Attorney, Agent, or Firm* — Jun He Law Offices P.C.; James J. Zhu

(57) ABSTRACT

The present disclosure provides compositions and methods useful for molecular and cellular separation, detection and quantification. The compositions provided herein comprise a nanostructure having magnetic property operably linked to an analyte-binding member.

29 Claims, 11 Drawing Sheets

(51) Int. Cl.
*G01N 33/58* (2006.01)
*B03C 1/01* (2006.01)
*B03C 1/30* (2006.01)
*B82Y 5/00* (2011.01)
*B82Y 15/00* (2011.01)

(52) U.S. Cl.
CPC ... *G01N 21/6486* (2013.01); *G01N 33/54326* (2013.01); *G01N 33/587* (2013.01); *B03C 2201/26* (2013.01); *B82Y 5/00* (2013.01); *B82Y 15/00* (2013.01); *C12Q 2563/155* (2013.01); *G01N 2446/00* (2013.01)

(56) References Cited

U.S. PATENT DOCUMENTS

| | | | | |
|---|---|---|---|---|
| 9,708,660 | B2* | 7/2017 | Fu | C12Q 1/6876 |
| 9,711,266 | B2* | 7/2017 | Fu | H01F 1/01 |
| 2004/0086885 | A1 | 5/2004 | Lee et al. | |
| 2006/0263906 | A1 | 11/2006 | Pang et al. | |
| 2006/0275850 | A1* | 12/2006 | Groome | C07K 16/26 |
| | | | | 435/7.92 |
| 2007/0212794 | A1 | 9/2007 | Tsukamoto et al. | |
| 2010/0008862 | A1 | 1/2010 | Fu et al. | |
| 2010/0112716 | A1 | 5/2010 | Rosenzweig et al. | |
| 2011/0059468 | A1 | 3/2011 | Earhart et al. | |
| 2015/0037249 | A1* | 2/2015 | Fu | A61K 47/48861 |
| | | | | 424/1.11 |
| 2015/0076392 | A1* | 3/2015 | Fu | A61K 49/0002 |
| | | | | 252/62.51 R |
| 2015/0212095 | A1* | 7/2015 | Fu | G01N 33/54326 |
| | | | | 435/7.92 |
| 2015/0252407 | A1* | 9/2015 | Fu | C12Q 1/6806 |
| | | | | 435/6.12 |
| 2016/0279270 | A1* | 9/2016 | Fu | A61K 49/0002 |
| 2017/0015975 | A1* | 1/2017 | Fu | C12N 5/0068 |

OTHER PUBLICATIONS

Sarawade et al., "Preparation of Hydrophobic mesoporous silica powder with a high specific surface area by surface modification of a wet-gel slurry and spray-drying", Powder Technology, vol. 197, pp. 288-294, published Oct. 17, 2009.*

Earhart C Met al., "Microfabricated magnetic sifter for high-throughput and high-gradient magnetic separation", Journal of Magnetism and Magnetic Materials vol. 321, No. 10, (Jan. 5, 2009), pp. 1436-1439.

Rosi Nathaniel L et al., "Nanostructures in Biodiagnositcs" Chemical Review (Jan. 4, 2005) vol. 105 No. 4, pp. 1547-1562.

Extended European search report for EP13770326.0.

* cited by examiner

MULTIFUNCTIONAL NANOPARTICLES FOR MOLECULAR AND CELLULAR SEPARATION, DETECTION AND QUANTIFICATION

CROSS-REFERENCE TO RELATED APPLICATIONS

The present application claims the benefit of U.S. Provisional Patent Application No. 61/618,779 filed on Mar. 31, 2012, which is incorporated herein by reference in its entirety.

FIELD OF THE INVENTION

The present invention is in the field of molecular and cellular detection in biological samples.

BACKGROUND

Current molecular and cellular detections are limited to methods such as ELISA or immunofluorescence. The advent of nanotechnology expands the molecular diagnostic field with enhanced sensitivity. Thus there are needs to develop and use nanotechnology or nanoparticles in detecting molecule and cells.

SUMMARY OF THE INVENTION

One aspect of the present disclosure relates to a composition comprising a nanostructure which contains a magnetic material and is operably linked to at least one analyte-binding member.

In certain embodiments, the nanostructure is colored or non-colored.

In certain embodiments, the colored nanostructure is bar-coded or associated with a detectable agent to show a color.

In certain embodiments, the detectable agent is a fluorescent molecule, a chemo-luminescent molecule, a bio-luminescent molecule, a radioisotope, a MRI contrast agent, a CT contrast agent, an enzyme-substrate label, or a coloring agent.

In certain embodiments, the magnetic material is a ferromagnetic material, a ferrimagnetic material, paramagnetic material, or a superparamagnetic material. In certain embodiments, the core nanoparticle comprises the magnetic material.

In certain embodiments, the analyte-binding member is selected from the groups consisting of Protein A; Protein G; a protein/peptide, an antibody or fragments thereof; a nuclei acid, a first molecular capable of specifically binding to a second molecule, carbohydrate, lipid, a polymer, or a small organic molecule; a ligand, a receptor, a guest chemical, and a host chemical.

In certain embodiments, the composition further comprises an analyte, wherein the analyte specifically binds to the analyte-binding member. The analyte can be selected from the group consisting of a biological sample, a cell, a virus, an antibody, a protein/peptide, a second nucleic acid; carbohydrate, lipid, a polymer, or a small organic molecule; a ligand, a receptor, a guest molecule, and a host molecule.

In certain embodiments, the composition further comprises a first signal indicator wherein the signal indicator contains a first analyte-binding member binding to the analyte and a first detectable signal. In certain embodiments, the first detectable signal is a first detectable agent or a non-magnetic colored nanoparticle.

In certain embodiments, the first analyte-binding member binds to a first epitope of the analyte, wherein the first epitope of the analyte do not substantially overlap with the epitope that the analyte-binding member of the nanoparticle binds to.

In certain embodiments, the composition further comprises a second signal indicator wherein the second signal indicator contains a second analyte-binding member binding to the analyte and a second detectable signal.

In certain embodiments, the second analyte-binding member binds to a second epitope of the analyte that do not substantially overlap with the epitope that the first analyte-binding member or that the analyte-binding member of the nanoparticle binds to. In certain embodiments, the second detectable signal is the same as the first detectable signal.

In certain embodiments, the composition further comprises a substrate having a magnetic grid wherein the colored magnetic nanoparticle is dispersed onto the magnetic grid.

The nanostructure provided herein can be any type of magnetic nanoparticles. In certain embodiments, a nanostructure refers to a nanostructure that has been disclosed in U.S. Prov. Appl. 61/589,777 and U.S. patent application Ser. No. 12/460,007 (all references cited in the present disclosure are incorporated herein in their entirety).

In certain embodiments, the nanostructure comprises at least one core nanoparticle embedded in or coated with a low density porous 3-D structure or coating, which is capable of carrying or associating with at least one bar-coding and/or detectable agent within or on the surface of the nanostructure.

In certain embodiments, the core nanoparticle comprises a nanoparticle or a cluster of nanoparticles. A single core nanoparticle may comprise a plurality or a cluster of mini-nanoparticles. The nanoparticles in the cluster may be made by the same composition, or different compositions.

In certain embodiments, the core nanoparticle includes, for example, a superparamagnetic iron oxide (SPIO) nanoparticle, or a non-SPIO nanoparticle. The non-SPIO nanoparticles include, for example, metallic nanoparticles (e.g., gold or silver nanoparticles), a metal oxide nanoparticle, semiconductor nanoparticle (e.g., quantum dots with individual or multiple components such as CdSe/ZnS, doped heavy metal free quantum dots or other semiconductor quantum dots); polymeric nanoparticles (e.g., particles made of one or a combination of PLGA (poly(lactic-co-glycolic acid), PCL (polycaprolactone), PEG (poly ethylene glycol) or other polymers); siliceous nanoparticles; and non-SPIO magnetic nanoparticles (e.g., MnFe2O4, SAF, and other types of magnetic nanoparticles). The core nanoparticle has a diameter ranging from about 1 nm to about 900 nm (preferably 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size).

In certain embodiments, the core nanoparticle has a shape of sphere, rod, tetrapod, pyramidal, multi-armed, nanotube, nanowire, nanofiber, or nanoplate.

In certain embodiments, the low density, porous 3-D structure refers to a structure with density at least 10 s times (e.g., 10 s times, 20 s times, 30 s times, 50 s times, 70 s times, 100 s times, 1000 s times, 10,000 times) lower than existing mesoporous materials (e.g., mesoporous materials having a pore size ranging from 2 nm to 50 nm). In certain embodiments, the low density, porous 3-D structure has a density of <1.0 g/cc (e.g., from 0.01 mg/cc to 1000 mg/cc). In certain embodiments, the density is determined using dry mass of the 3-D structure divided by the total volume of such 3-D structure in an aqueous solution.

In certain embodiments, the low density, porous 3-D structure is highly porous. Such low density structure further refers to a structure having at least 40% to at least 99.9% (preferably 50% to 99.9%) of empty space or porosity in the structure. In certain embodiments, at least 80% of the pores having size of 1 nm to 500 nm in pore radius.

In certain embodiments, the low density, porous 3-D structure is a structure that can not be obviously observed or substantially invisible under transmission electron microscope, for example, even when the feature size of the low density structure is in the 10 s or 100 s nanometer range.

In certain embodiments, the low density, porous 3-D structure is made of silicon-containing molecules (e.g., silanes, organosilanes, alkoxysilanes, silicates and derivatives thereof). For example, the silicon-containing molecules can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis[3-(triethoxysilyl)propyl]-tetrasulfide, Bis-[3-(triethoxysilyl)propyl]-disulfide, aminopropyltriethoxysilane, N-2-(aminoethyl)-3-amino propyltrimethoxysilane, Vinyltrimethoxysilane, Vinyl-tris (2-methoxyethoxy) silane, 3-methacryloxypropylt-rimethoxy silane, 2-(3,4-epoxycyclohexy)-ethyl trimethoxysilane, 3-glycidoxy-propyltriethoxysilane, 3-isocyanatopropyltriethoxysilane, 3-cyanatopropyltriethoxysilane, and sodium silicates.

In certain embodiments, the low density, porous 3-D structure is associated with the core nanoparticle via intra-molecular interaction (e.g., covalent bonds, metallic bonds, and/or ionic bonding) or inter-molecular interaction (e.g., hydrogen bond, and/or non covalent bonds).

In certain embodiments, the low density, porous 3-D structure is a stable crosslinked coating with thickness ranging from 1 nm to 1000 nm (e.g., from 1 nm to 500 nm). In certain embodiments, the thickness of the low density, porous 3-D structure is controllable, so is the number of bar-coding and/or detectable agents that could be carried.

Another aspect of the present disclosure relates to multiplex systems comprising a first magnetic nanoparticle having a first analyte-binding member capable of binding to a first analyte and a second magnetic nanoparticle having a second analyte-binding member capable of binding to a second analyte.

Another aspect of the present disclosure relates to methods of determining the presence and/or quantity of an analyte in a sample comprising the steps of a) contacting the sample with the composition provided herein in a mixture; and b) detecting and quantifying the co-location of the color of the colored magnetic nanoparticle and the analyte.

Another aspect of the present disclosure relates to methods of determining the presence and/or quantity of an analyte in a sample comprising the steps of a) contacting the sample with the composition provided herein to form a mixture; b) dispersing the mixture onto a magnetic grid; and c) detecting and quantifying the detectable signal of the signal indicator.

Another aspect of the present disclosure relates to methods of determining the presence and/or quantity of an analyte in a sample comprising the steps of a) contacting the sample with the composition provided herein; b) measuring the presence and/or quantity of an analyte.

Another aspect of the present disclosure relates to methods of determining the presence and/or quantity of a first analyte and a second analyte in a sample comprising the steps of a) contacting the sample with the multiplex system provided herein to form a mixture; b) dispersing the mixture onto a magnet grid; and c) measuring the presence and/or quantity of the analytes.

Another aspect of the present disclosure relates to methods of determining the presence and/or quantity of a first analyte and a second analyte in a sample comprising the steps of a) contacting the sample with the multiplex system provided herein; and b) measuring the presence and/quantity of the analytes.

Another aspect of the present disclosure relates to methods of determining the presence and/or quantity of an analyte in a sample comprising the steps of a) contacting the sample with the composition of provided herein to form a mixture; b) loading the mixture to a loading region of a lateral flow test strip, wherein the test strip comprises a detection region comprising an immobilized first analyte-binding member; and c) detecting and/or quantifying the analyte at the detection region of the test strip.

DESCRIPTION OF THE DRAWINGS

In FIG. 2(A), a colored magnetic nanostructure captures the analyte through the analyte-binding member and the captured analyte is bounded to a signal indicator. The signal indicator binds to the captured analyte (e.g., an antibody to the analyte or having a second analyte-binding member) and having a detectable agent. The magnetic nanostructure complexes are dispersed onto a substrate having a magnetic grid. After washing, the detection of the detectable agent indicates the presence and amount of the analyte. In FIG. 2(B), two signal indicators bind to the captured analyte at distinct epitopes of the analyte. An analyte is bounded or captured by a magnetic nanoparticle via the analyte binding member of the magnetic nanoparticle. A first signal indicator comprises a first analyte binding member (binding to the captured analyte) and a first detectable signal. A second signal indicator comprises a second analyte-binding member (binding to the captured analyte) and a second detectable signal. The first and second signal can be the same or different kinds Examples of the binding interactions include but not limited to antigen-antibody, or nucleic acids interactions.

In FIG. 3(A), multiple magnetic nanoparticles with or without color capture specifically multiple analytes through the interaction of the analyte binding member on the magnetic nanoparticle surface and each specific analyte. Different signal indicators then bind to different analyte to identify multiple analytes in the sample. In FIG. 3(B), multiple magnetic nanoparticles with or without color bind to multiple analyte through specific interactions of the nanoparticle surface analyte binding members and the analyte, and then multiple signal indicators could bind to multiple epitopes of each analyte, respectively, for multiplexed analyte identification. Each of the three analytes is captured by the respective magnetic nanostructure, and the captured analytes are bounded to their respective signal indicators. In FIG. 3(C), with the assistant of a magnetizable grid, these magnetic nanostructures could react with the analyte molecules in the solution, then flow through the magnetizable grid and being captured. Another molecule will subsequently interact with the analyte and generate a signal (blue). The multiplexed color of fluorescent magnetic nanostructures when present could be used to code the surface capture molecule such as antibody or a nucleic acid strand, and the blue color prove the existence of the capture event. The signal indicator could also be introduced into the solution with the magnetic nanoparticles and the analytes, all molecular interactions could be accomplished in solution, and then the solution will flow through a magnetic grid to spread the sample onto a surface for identification.

DETAILED DESCRIPTION OF THE INVENTION

Figure 1:
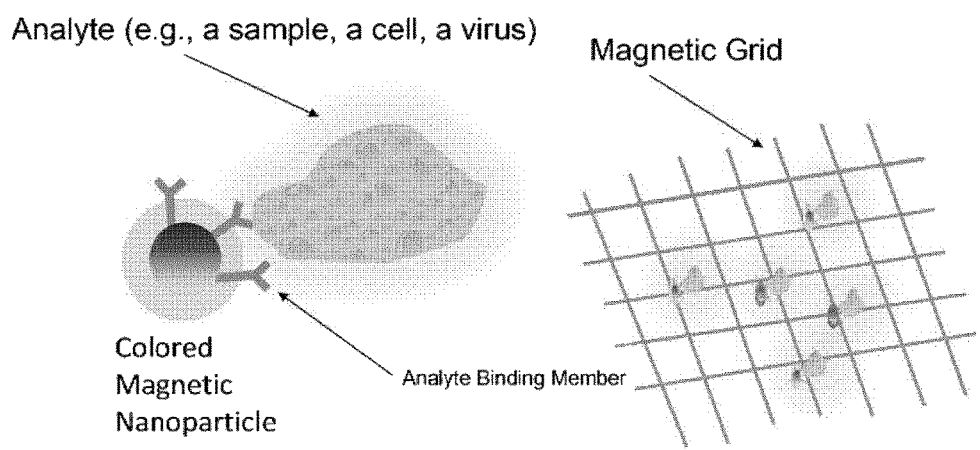
FIG. 1 is a schematic drawing of a method for analyte separation and identification. For cell separation and identification that allow direct recognition of the presence of the analyte, fluorescent magnetic nanostructures can be conveniently used. The reaction is solution based, then the magnetic grid is applied, presence of co-localization of signal and cell indicate that there are specific cell markers that interact with the specific biomolecule on nanostructure surface. Different color of nanostructure can be used to identify different cell markers, different types of cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, solid state chemistry, inorganic chemistry, organic chemistry, physical chemistry, analytical chemistry, materials chemistry, biochemistry, biology, molecular biology, recombinant DNA techniques, pharmacology, imaging, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

The following embodiments are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Composition

One aspect of the present disclosure relates to a composition comprising a nanostructure and an analyte-binding member.

The term "nanostructure" as used herein, refers to a particle having a diameter ranging from about 1 nm to about 1500 nm (e.g. from 1 nm to 1200 nm, from 1 nm to 1000 nm, from 1 nm to 800 nm, from 1 nm to 500 nm, from 1 nm to 400 nm, etc.). In certain embodiments, the nanostructure comprises a single particle or a cluster of particles. In certain embodiments, the nanostructure comprises a core nanoparticle and a coating. The core nanoparticle can be a single or a cluster of particles. The coating can be any coating known in the art, for example, a polymer coating such as polyethylene glycol, silane, and polysaccharides (e.g. dextran and its derivatives).

The nanostructures provided herein contain a magnetic material. Suitable magnetic materials include, for example, ferrimagnetic or ferromagnetic materials (e.g., iron, nickel, cobalt, some alloys of rare earth metals, and some naturally occurring minerals such as lodestone), paramagnetic materials (such as platinum, aluminum), and superparamagnetic materials (e.g., superparamagnetic iron oxide or SPIO).

The magnetic material has magnetic property which allows the nanostructure to be pulled or attracted to a magnet or in a magnetic field. Magnetic property can facilitate manipulation (e.g., separation, purification, or enrichment) of the nanostructures using magnetic interaction. The magnetic nanostructures can be attracted to or magnetically guided to an intended site when subject to an applied magnetic field, for example a magnetic field from high-filed and/or high-gradient magnets. For example, a magnet (e.g., magnetic grid) can be placed in the proximity of the nanostructures so as to attract the magnetic nanostructures.

The nanostructure is operably linked to at least one analyte-binding member. The term "operably linked" as used herein, includes embedding, incorporating, integrating, binding, attaching, combining, cross-linking, mixing, and/or coating the analyte-binding member to the nanostructure. The analyte-binding member can be operably linked to the nanostructure through non-covalent association (e.g., hydrogen bonds, ionic bonds, van der Waals forces, and hydrophobic interaction) or covalent binding. For example, the analyte-binding member mixed with and/or incorporated onto the surface of the nanostructure, or can also be loaded to the pores of the nanostructure.

In certain embodiments, the analyte-binding members are molecules capable of capturing or specifically binding to an analyte. "Capturing", "binding" or "specifically binding" as used herein, means a non-random binding interaction between two molecules. The specific binding can be characterized by binding affinity (Kd), which is calculated as the ratio of dissociation rate to association rate ($k_{off}/k_{on}$) when the binding between the two molecules reaches equilibrium. The dissociation rate ($k_{off}$) measured at the binding equilibrium may also be used when measurement of $k_{on}$ is difficult to obtain, for example, due to aggregation of one molecule. The analyte-binding affinity (e.g., $K_D$ or $k_{off}$) can be appropriately determined using suitable methods known in the art, including, for example, Biacore (see, for example, Murphy, M. et al, Current protocols in protein science, Chapter 19, unit 19.14, 2006) and Kinexa techniques (see, for example, Darling, R. J., et al, Assay Drug Dev. Technol., 2(6): 647-657 (2004)).

Examples of analyte-binding members include Protein A; Protein G; antigen-binding members (e.g., antibodies or fragments thereof); nuclei acid (or a fragment of nuclei acid, an oligo nucleotide); or a protein/peptide binding specifically to a molecule such as another protein/peptide, an antibody, a piece of nuclei acid (DNA or RNA), carbohydrate, lipid, a polymer, or a small organic molecule such as a drug; a ligand (e.g., a peptide, small molecule, hormone, a drug, toxin, neurotransmitter) that specifically binds to a receptor, or a receptor that specifically binds to a ligand, a chemical in a supermolecular structure (e.g., host-guest chemistry complex such as a p-xylylenediammonium bound within a cucurbituril) whereas the chemical is a host molecule (e.g., cyclodextrins, calixarenes, cucurbiturils, porphyrins, metallacrowns, crown ethers, zeolites, cyclotriveratrylenes, cryptophanes and carcerands) or a guest molecule (e.g., prostaglandin, itraconazole).

In certain embodiments, the analyte is a substance that specifically interacts or binds to the analyte-binding member. Example of analytes include a sample, a biological sample, a cell (e.g. an antibody producing hybridoma cell, a circulating tumor cell, a cell expressing a disease marker, etc.), a virus, an antibody, a protein/peptide, a nuclei acid (DNA or RNA, fragment thereof, an oligonucleotide, complimentary to the capturing member nuclei acid); carbohydrate, lipid, a polymer, or a small organic molecule such as a drug; a ligand that specifically binds to a receptor as an analyte-binding member, a receptor that specifically binds to a ligand as an analyte-binding member, a guest molecule that specifically interacts with a host molecule or vice versa.

A nanostructure can be operably linked to a suitable amount of the analyte binding member. The ratio of the nanostructure to the analyte binding member can be appropriately adjusted by people skilled in the art according to the specific needs. For example, the ratio of the nanostructures to the analyte binding member can be increased for detection of a low amount of the analyte.

In certain embodiments, the composition may further comprise an analyte specifically bound to the analyte binding member.

Nanostructure

Any nanostructures having a magnetic property known in the art can be used.

In certain embodiments, the nanostructure provided herein comprises a magnetic nanoparticle which comprises a magnetic material. For example, the magnetic nanoparticle of the nanostructure is a superparamagnetic iron oxide (SPIO) nanoparticle.

The SPIO nanoparticle is an iron oxide nanoparticle, either maghemite ($\gamma$-$Fe_2O_3$) or magnetite ($Fe_3O_4$), or nanoparticles composed of both phases. The SPIO can be synthesized with a suitable method and dispersed as a colloidal solution in organic solvents or water. Methods to synthesize the SPIO nanoparticles are known in the art (see, for example, Morteza Mahmoudi et al, Superparamagnetic Iron Oxide Nanoparticles: Synthesis, Surface Engineering, Cytotoxicity and Biomedical Applications, published by Nova Science Pub Inc, 2011). In one embodiment, the SPIO nanoparticles can be made through wet chemical synthesis methods which involve co-precipitation of $Fe^{2+}$ and $Fe^{3+}$ salts in the presence of an alkaline medium. During the synthesis, nitrogen may be introduced to control oxidation, surfactants and suitable polymers may be added to inhibit agglomeration or control particle size, and/or emulsions (such as water-in-oil microemulsions) may be used to modulate the physical properties of the SPIO nanoparticle (see, for example, Jonathan W. Gunn, The preparation and characterization of superparamagnetic nanoparticles for biomedical imaging and therapeutic application, published by ProQuest, 2008). In another embodiment, the SPIO nanoparticles can be generated by thermal decomposition of iron pentacarbonyl, alone or in combination with transition metal carbonyls, optionally in the presence of one or more surfactants (e.g., lauric acid and oleic acid) and/or oxidants (e.g., trimethylamine-N-oxide), and in a suitable solvent (e.g., dioctyl ether or hexadecane) (see, for example, US patent application 20060093555). In another embodiment, the SPIO nanoparticles can also be made through gas deposition methods, which involves laser vaporization of iron in a helium atmosphere containing different concentrations of oxygen (see, Miller J. S. et al., Magnetism: Nano-sized magnetic materials, published by Wiley-VCH, 2002). In certain embodiments, the SPIO nanoparticles are those disclosed in US patent application US20100008862.

In certain embodiments, the nanostructure can further comprise a non-SIPO nanoparticle.

The non-SPIO nanoparticles include, for example, metallic nanoparticles (e.g., gold or silver nanoparticles (see, e.g., Hiroki Hiramatsu, F. E. O., Chemistry of Materials 16, 2509-2511 (2004)), semiconductor nanoparticles (e.g., quantum dots with individual or multiple components such as CdSe/ZnS (see, e.g., M. Bruchez, et al., science 281, 2013-2016 (1998))), doped heavy metal free quantum dots (see, e.g., Narayan Pradhan et al, J. Am. chem. Soc. 129, 3339-3347 (2007)) or other semiconductor quantum dots); polymeric nanoparticles (e.g., particles made of one or a combination of PLGA (poly(lactic-co-glycolic acid) (see, e.g., Minsoung Rhee et al., Adv. Mater. 23, H79-H83 (2011)), PCL (polycaprolactone) (see, e.g., Marianne Labet et al., Chem. Soc. Rev. 38, 3484-3504 (2009)), PEG (poly ethylene glycol) or other polymers); siliceous nanoparticles; and non-SPIO magnetic nanoparticles (e.g., $MnFe_2O_4$ (see, e.g., Jae-Hyun Lee et al., Nature Medicine 13, 95-99 (2006)), synthetic antiferromagnetic nanoparticles (SAF) (see, e.g., A. Fu et al., Angew. Chem. Int. Ed. 48, 1620-1624 (2009)), and other types of magnetic nanoparticles).

In certain embodiments, the non-SPIO nanoparticle is a colored nanoparticle, for example, a semiconductor nanoparticle such as a quantum dot.

The non-SPIO nanoparticles can be prepared or synthesized using suitable methods known in the art, such as for example, sol-gel synthesis method, water-in-oil micro-emulsion method, gas deposition method and so on. For example, gold nanoparticles can be made by reduction of chloroaurate solutions (e.g., $HAuCl_4$) by a reducing agent such as citrate, or acetone dicarboxylate. For another example, CdS semiconductor nanoparticle can be prepared from $Cd(ClO_4)_2$ and $Na_2S$ on the surface of silica particles. For another example, II-VI semiconductor nanoparticles can be synthesized based on pyrolysis of organometallic reagents such as dimethyl cadmium and trioctylphosphine selenide, after injection into a hot coordinating solvent (see, e.g., Günter Schmid, Nanoparticles: From Theory to Application, published by John Wiley & Sons, 2011). Doped heavy metal free quantum dots, for example Mn-doped ZnSe quantum dots can be prepared using nucleation-doping strategy, in which small-sized MnSe nanoclusters are formed as the core and ZnSe layers are overcoated on the core under high temperatures. For another example, polymeric nanoparticles can be prepared by emulsifying a polymer in a two-phase solvent system, inducing nanosized polymer droplets by sonication or homogenization, and evaporating the organic solvent to obtain the nanoparticles. For another example, siliceous nanoparticles can be prepared by sol-gel synthesis, in which silicon alkoxide precursors (e.g., TMOS or TEOS) are hydrolyzed in a mixture of water and ethanol in the presence of an acid or a base catalyst, the hydrolyzed monomers are condensed with vigorous stirring and the resulting silica nanoparticles can be collected. For another example, SAFs, a non-SPIO magnetic nanoparticle, can be prepared by depositing a ferromagnetic layer on each of the two sides of a nonmagnetic space layer (e.g., ruthenium metal), along with a chemical etchable copper release layer and protective tantalum surface layers, using ion-bean deposition in a high vacuum, and the SAF nanoparticle can be released after removing the protective layer and selective etching of copper.

The size of the nanoparticles ranges from 1 nm to 100 nm in size (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size). The size of nanoparticles can be controlled by selecting appropriate synthesis methods and/or systems. For example, to control the size of nanoparticles, synthesis of nanoparticles can be carried out in a polar solvent which provides ionic species that can adsorb on the surface of the nanoparticles, thereby providing electrostatic effect and particle-particle repulsive force to help stabilize the nanoparticles and inhibit the growth of the nanoparticles. For another example, nanoparticles can be synthesized in a micro-heterogeneous system that allows compartmentalization of nanoparticles in constrained cavities or domains. Such a micro-heterogeneous system may include, liquid crystals, mono and multilayers, direct micelles, reversed micelles, microemulsions and vesicles. To obtain nanoparticles within a desired size range, the synthesis conditions may be properly controlled or varied to provide for, e.g., a desired solution concentration or a desired cavity range (a detailed review can be found at, e.g., Vincenzo Liveri, Controlled synthesis of nanoparticles in microheterogeneous systems, Published by Springer, 2006).

The shape of the nanoparticles can be spherical, cubic, rod shaped (see, e.g., A. Fu et al., *Nano Letters,* 7, 179-182 (2007)), tetrapo-shaped (see, e.g., L. Manna et al., *Nature Materials,* 2, 382-385 (2003)), pyramidal, multi-armed, nanotube, nanowire, nanofiber, nanoplate, or any other suitable shapes. Methods are known in the art to control the shape of the nanoparticles during the preparation (see, e.g., Waseda Y. et al., Morphology control of materials and nanoparticles: advanced materials processing and characterization, published by Springer, 2004). For example, when the nanoparticles are prepared by the bottom-up process (i.e. from molecule to nanoparticle), a shape controller which adsorbs strongly to a specific crystal plane may be added to control the growth rate of the particle.

A single nanostructure may comprise a single nanoparticle or a plurality or a cluster of mini-nanoparticles (A. Fu et al., *J. Am. chem. Soc.* 126, 10832-10833 (2004), J. Ge et al., *Angew. Chem. Int. Ed.* 46, 4342-4345 (2007), Zhenda Lu et al., *Nano* Letters 11, 3404-3412 (2011).). The mini-nanoparticles can be homogeneous (e.g., made of the same composition/materials or having same size) or heterogeneous (e.g., made of different compositions/materials or having different sizes). A cluster of homogeneous mini-nanoparticles refers to a pool of particles having substantially the same features or characteristics or consisting of substantially the same materials. A cluster of heterogeneous mini-nanoparticles refers to a pool of particles having different features or characteristics or consisting of substantially different materials. For example, a heterogeneous mini-nanoparticle may comprise a quantum dot in the center and a discrete number of gold (Au) nanocrystals attached to the quantum dot. When the nanoparticles are associated with a coating (as described below), different nanoparticles in a heterogeneous nanoparticle pool do not need to associate with each other at first, but rather, they could be individually and separately associated with the coating.

In certain embodiments, a nanostructure disclosed comprises a plurality of nanoparticles. For example, the nanostructure contains 2, 3, 4, 5, 6, 7, 8, 9, 10, 11, 12, 13, 14, 15, 16, 17, 18, 19, 20, 25, 30, 35, 40, 50, 60, 70, 80, 90, 100, 100 s or 1000 s nanoparticles.

In certain embodiments, the nanostructure provided herein further comprises a coating. At least one core nanoparticle can be embedded in or coated with the coating. Any suitable coatings known in the art can be used, for example, a polymer coating and a non-polymer coating.

The coating interacts with the core nanoparticles through 1) intra-molecular interaction such as covalent bonds (e.g., Sigma bond, Pi bond, Delta bond, Double bond, Triple bond, Quadruple bond, Quintuple bond, Sextuple bond, 3c-2e, 3c-4-e, 4c-2e, Agostic bond, Bent bond, Dipolar bond, Pi backbond, Conjugation, Hyperconjugation, Aromaticity, Hapticity, and Antibonding), metallic bonds (e.g., chelating interactions with the metal atom in the core nanoparticle), or ionic bonding (cation it-bond and salt bond), and 2) inter-molecular interaction such as hydrogen bond (e.g., Dihydrogen bond, Dihydrogen complex, Low-barrier hydrogen bond, Symmetric hydrogen bond) and non covalent bonds (e.g., hydrophobic, hydrophilic, charge-charge, or π-stacking interactions, van der Waals force, London dispersion force, Mechanical bond, Halogen bond, Aurophilicity, Intercalation, Stacking, Entropic force, and chemical polarity).

In certain embodiments, the coating comprises a low density, porous 3-D structure, as disclosed in U.S. Prov. Appl. 61/589,777 and U.S. patent application Ser. No. 12/460,007 (all references cited in the present disclosure are incorporated herein in their entirety).

The low density, porous 3-D structure refers to a structure with density much lower (e.g., 10 s times, 20 s times, 30 s times, 50 s times, 70 s times, 100 s times) than existing mesoporous nanoparticles (e.g., mesoporous nanoparticles having a pore size ranging from 2 nm to 50 nm). (A. Vincent, et. al., J. Phys. Chem. C, 2007, 111, 8291-8298. J. E. Lee, et. al., J. Am. Chem. Soc., 2010, 132, 552-557. Y.-S. Lin, et. al., J. Am. Chem. Soc., 2011, 133, 20444-20457. Z. Lu, Angew. Chem. Int. Ed., 2010, 49, 1862-1866.)

In certain embodiments, the low density, porous 3-D structure refers to a structure having a density of <1.0 g/cc (e.g., <100 mg/cc, <10 mg/cc, <5 mg/cc, <1 mg/cc, <0.5 mg/cc, <0.4 mg/cc, <0.3 mg/cc, <0.2 mg/cc, or <0.1 mg/cc) (for example, from 0.01 mg/cc to 10 mg/cc, from 0.01 mg/cc to 8 mg/cc, from 0.01 mg/cc to 5 mg/cc, from 0.01 mg/cc to 3 mg/cc, from 0.01 mg/cc to 1 mg/cc, from 0.01 mg/cc to 1 mg/cc, from 0.01 mg/cc to 0.8 mg/cc, from 0.01 mg/cc to 0.5 mg/cc, from 0.01 mg/cc to 0.3 mg/cc, from 0.01 mg/cc to 1000 mg/cc, from 0.01 mg/cc to 915 mg/cc, from 0.01 mg/cc to 900 mg/cc, from 0.01 mg/cc to 800 mg/cc, from 0.01 mg/cc to 700 mg/cc, from 0.01 mg/cc to 600 mg/cc, from 0.01 mg/cc to 500 mg/cc, from 0.1 mg/cc to 800 mg/cc, from 0.1 mg/cc to 700 mg/cc, from 0.1 mg/cc to 1000 mg/cc, from 1 mg/cc to 1000 mg/cc, from 5 mg/cc to 1000 mg/cc, from 10 mg/cc to 1000 mg/cc, from 20 mg/cc to 1000 mg/cc, from 30 mg/cc to 1000 mg/cc, from 30 mg/cc to 1000 mg/cc, from 30 mg/cc to 900 mg/cc, from 30 mg/cc to 800 mg/cc, or from 30 mg/cc to 700 mg/cc).

The density of 3-D structure can be determined using various methods known in the art (see, e.g., Lowell, S. et al., Characterization of porous solids and powders: surface area, pore size and density, published by Springer, 2004). Exemplary methods include, Brunauer Emmett Teller (BET) method and helium pycnometry (see, e.g., Varadan V. K. et al., Nanoscience and Nanotechnology in Engineering, published by World Scientific, 2010). Briefly, in BET method, dry powders of the testing 3-D structure is placed in a testing chamber to which helium and nitrogen gas are fed, and the change in temperature is recorded and the results are analyzed and extrapolated to calculate the density of the testing sample. In helium pycnometry method, dry powders of the testing 3-D structure are filled with helium, and the helium pressure produced by a variation of volume is studied to provide for the density. The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the 3-D structure is fully extended in a buffer solution.

In certain embodiments, the density of the 3-D structure can be determined using the dry mass of the 3-D structure divided by the total volume of such 3-D structure in an aqueous solution. For example, dry mass of the core particles with and without the 3-D structure can be determined respectively, and the difference between the two would be the total mass of the 3-D structure. Similarly, the volume of a core particle with and without the 3-D structure in an aqueous solution can be determined respectively, and the difference between the two would be the volume of the 3-D structure on the core particle in an aqueous solution.

In certain embodiments, the porous nanostructure can be dispersed as multiple large nanoparticles coated with the 3-D structure in an aqueous solution, in such case, the total volume of the 3-D structure can be calculated as the average volume of the 3-D structure for an individual large nanoparticle multiplied with the number of the large nanoparticles.

For each individual large nanoparticle, the size (e.g., radius) of the particle with 3-D structure can be determined with Dynamic Light Scattering (DLS) techniques, and the size (e.g., radius) of the particle core without the 3-D structure can be determined under Transmission Electron Microscope (TEM), as the 3-D structure is substantially invisible under TEM. Accordingly, the volume of the 3-D structure on an individual large nanoparticle can be obtained by subtracting the volume of the particle without 3-D structure from the volume of the particle with the 3-D structure.

The number of large nanoparticles for a given core mass can be calculated using any suitable methods. For example, an individual large nanoparticle may be composed of a plurality of small nanoparticles which are visible under TEM. In such case, the average size and volume of a small nanoparticle can be determined based on measurements under TEM, and the average mass of a small nanoparticle can be determined by multiplying the known density of the core material with the volume of the small particle. By dividing the core mass with the average mass of a small nanoparticle, the total number of small nanoparticles can be estimated. For an individual large nanoparticle, the average number of small nanoparticles in it can be determined under TEM. Accordingly, the number of large nanoparticles for a given core mass can be estimated by dividing the total number of small nanoparticles with the average number of small nanoparticles in an individual large nanoparticle.

Alternatively, the low density, porous 3-D structure refers to a structure having 40%-99.9% (preferably 50% to 99.9%) of empty space or pores in the structure, where 80% of the pores having size of 1 nm to 500 nm in pore radius.

The porosity of the 3-D structure can be characterized by the Gas/Vapor adsorption method. In this technique, usually nitrogen, at its boiling point, is adsorbed on the solid sample. The amount of gas adsorbed at a particular partial pressure could be used to calculate the specific surface area of the material through the Brunauer, Emmit and Teller (BET) nitrogen adsorption/desorption equation. The pore sizes are calculated by the Kelvin equation or the modified Kelvin equation, the BJH equation (see, e.g., D. Niu et al., *J. Am. chem. Soc.* 132, 15144-15147 (2010)).

The porosity of the 3-D structure can also be characterized by mercury porosimetry (see, e.g., Varadan V. K. et al., supra). Briefly, gas is evacuated from the 3-D structure, and then the structure is immersed in mercury. As mercury is non-wetting at room temperature, an external pressure is applied to gradually force mercury into the sample. By monitoring the incremental volume of mercury intruded for each applied pressure, the pore size can be calculated based on the Washburn equation.

Alternatively, the low density, porous 3-D structure refers to a structure that has a material property, that is, the porous structure (except to the core nanoparticle or core nanoparticles) could not be obviously observed or substantially transparent under transmission electron microscope, for example, even when the feature size of the 3-D structure is in the 10 s or 100 s nanometer range. The term "obviously observed" or "substantially transparent" as used herein means that, the thickness of the 3-D structure can be readily estimated or determined based on the image of the 3-D structure under TEM. The nanostructure (e.g., nanoparticles coated with or embedded in/on a low density porous 3-D structure) can be observed or measured by ways known in the art. For example, the size (e.g., radius) of the nanostructure with the 3-D structure can be measured using DLS methods, and the size (e.g., radius) of the core particle without the 3-D structure can be measured under TEM. In certain embodiments, the thickness of the 3-D structure is measured as 10 s, 100 s nanometer range by DLS, but cannot be readily determined under TEM. For example, when the nanostructures provided herein are observed under Transmission Electron Microscope (TEM), the nanoparticles can be identified, however, the low density porous 3-D structure can not be obviously observed, or is almost transparent (e.g., see FIGS. 2 and 3). This distinguishes the nanostructures provided herein from those reported in the art (see, FIG. 4) that comprise nanoparticles coated with crosslinked and size tunable 3-D structure, including the mesoporous silica nanoparticles or coating (see, e.g., J. Kim, et. al., J. Am. Chem. Soc., 2006, 128, 688-689; *J.* Kim, et. al., Angew. Chem. Int. Ed., 2008, 47, 8438-8441). This feature also indicates that the low density porous 3-D structure provided herein has a much lower density and/or is highly porous in comparison to other coated nanoparticles known in the art.

The porosity of the 3-D structure can be further evaluated by the capacity to load different molecules (see, e.g., Wang L. et al., *Nano Research* 1, 99-115 (2008)). As the 3-D structure provided herein has a low density, it is envisaged that more payload can be associated with the 3-D structure than with other coated nanoparticles (see, e.g., FIG. 1). For example, when 3-D structure is loaded with organic fluorophores such as Rhodamin, over $10^5$ Rhodamin molecules can be loaded to 3-D structure of one nanoparticle.

In certain embodiments, the low density structure refers to a structure capable of absorbing or carrying a fluorescent payload whose fluorescence intensity is at least 100 fold of that of the free fluorescent molecule (e.g., at least 150 fold, 200 fold, 250 fold, 300 fold, 350 fold, 400 fold, 450 fold, 500 fold, 550 fold or 600 fold). The fluorescence intensity of a loaded nanoparticle can be quantified under the same excitation and emission wave lengths as that of the fluorescent molecules. The fluorescence intensity of the loaded low density structure indicates the payload of the fluorescent molecule, and also indirectly reflects the porosity of the low density structure.

In certain embodiments, the low density, porous 3-D structure is made of silane-containing or silane-like molecules (e.g., silanes, organosilanes, alkoxysilanes, silicates and derivatives thereof).

In certain embodiments, the silane-containing molecule comprises an organosilane, which is also known as silane coupling agent. Organosilane has a general formula of $R_xSiY_{(4-x)}$, wherein R group is an alkyl, aryl or organofunctional group. Y group is a methoxy, ethoxy or acetoxy group. x is 1, 2 or 3. The R group could render a specific function such as to associate the organosilane molecule with the surface of the core nanoparticle or other payloads through covalent or non-covalent interactions. The Y group is hydrolysable and capable of forming a siloxane bond to crosslink with another organosilane molecule. Exemplary R groups include, without limitation, disulphidealkyl, aminoalkyl, mercaptoalkyl, vinylalkyl, epoxyalkyl, and methacrylalkyl, carboxylalkyl groups. The alkyl group in an R group can be methylene, ethylene, propylene, and etc. Exemplary Y groups include, without limitation, alkoxyl such as $OCH_3$, $OC_2H_5$, and $OC_2H_4OCH_3$. For example, the organosilane can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis-[3-(triethoxysilyl)propyl]-tetrasulfide, Bis-[3-(triethoxysilyl)propyl]-disulfide, aminopropyltriethoxysilane, N-2-(aminoethyl)-3-amino propyltrimethoxysilane, Vinyltrimethoxysilane, Vinyl-tris (2-methoxyethoxy)silane, 3-methacryloxypropyltrimethoxy silane, 2-(3,4-epoxycyclohexy)-ethyl trimethoxysilane, 3-glycidoxy-propyltriethoxysilane, 3-isocyanatopropyltriethoxysilane, and 3-cyanatopropyltriethoxysilane.

Colored Nanostructure

The nanostructures provided herein can be colored or non-colored. "Colored" as used herein, means that the nanostructure is capable of generating a color signal under a suitable condition. For example, the colored nanostructure may emit a fluorescent color signal upon excitation with a light of a certain wave length. The nanostructures may alternatively be non-colored. A non-colored nanostructure does not emit a color signal when subject to a condition that would otherwise induce a color signal for a colored nanostructure.

In certain embodiments, a colored nanostructure is barcoded or associated with a detectable agent to show color. The term "bar-coding" or "bar-coded" or "IDed" means that the nanostructure is associated with a known code or a known label that allows identification of the nanostructure. "Code" as used herein, refers to a molecule capable of generating a detectable signal that distinguishes one barcoded or IDed nanostructure from another. For example, the colored nanostructure may comprise a colored nanoparticle (e.g. a quantum dot) which emits a detectable color signal at a known wave length.

In certain embodiments, the characteristics or the identity of a bar-coded nanostructure is based on multiplexed optical coding system as disclosed in Han et al., Nature Biotechnology, Vol. 19, pp: 631-635 (2001) or U.S. patent application Ser. No. 10/185,226. Briefly, multicolor semiconductor quantum-dots (QDs) are embedded in the nanostructure. For each QD, there is a given intensity (within the levels of, for example. 0-10) and a given color (wavelength). For each single color coding, the nanostructure has different intensity of QDs depending on the number of QDs embedded therein. If QDs of multiple colors (n colors) and multiple intensity (m levels of intensity) are used, then the nanostructures may have a total number of unique identities or codes, which is equal to m to the exponent of m less one ($m^n-1$). In addition, since the porous structure can be associated with additional payloads (e.g., fluorescent organic molecules). If there are Y number of additional fluorescent colors available, the total number of code can be $Y \times (m^n-1)$.

In certain embodiments, the nanostructure (with or without bar-coding) is colored by being operably linked to a detectable agent. A detectable agent can be a fluorescent molecule, a chemo-luminescent molecule, a bio-luminescent molecule, a radioisotope, a MRI contrast agent, a CT contrast agent, an enzyme-substrate label, and/or a coloring agent etc.

Examples of fluorescent molecules include, without limitation, fluorescent compounds (fluorophores) which can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs-AutoFluorescent Protein— (Quantum Biotechnologies); Alexa® Fluor 350; Alexa® Fluor 405; Alexa® Fluor 500; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DID S; Dihydrorhodamine 123 (DHR); DiI (DiIC18(3)); Dinitrophenol; DiO (DiOC18 (3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/ Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/ Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE], Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), fluorescent semiconductor nanostructures, lanthanides or combinations thereof.

Examples of radioisotopes include, $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$, $^{18}F$, $^{201}Tl$, $^{67}Ga$, $^{137}Cs$ and other radioisotopes.

Examples of enzyme-substrate labels include, luciferases (e.g., firefly luciferase and bacterial luciferase), luciferin, 2,3-dihydrophthalazinedionesm, alate dehydrogenase, urease, peroxidase such as horseradish peroxidase (HRPO), alkaline phosphatase, -galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Sample Complex and Methods of Use

Another aspect of the present disclosure relates to a sample complex, comprising a nanostructure disclosed herein with an analyte-binding member and an analyte or a sample (when a sample is an analyte such as a cell, a virus) wherein the sample binds to the nanostructure. As shown in FIG. 1, the analyte binding member is a molecule (e.g., antibody) that specifically binds to surface of the sample (e.g., a sample specific antigen) so that the binding will lead to the detection of the presence and purification of the sample as the analyte-binding member specifically binds to such a sample but not other samples. The complex structure further comprises a magnetic grid (either on a substrate or in solution), so that the nanostructure binding to the sample can be dispersed on the grid and co-location of the colored nanostructure or the color and the sample (e.g., through microscope) indicates the presence of a sample specifically binding to a specific analyte which is reflected by the bar-code or color or fluorescence of the nanostructure. Once a plurality of these complexes (containing different types of biological samples and different corresponding colored nanostructures) are dispersed on the grid, each individual sample can be detected and isolated as well. It is contemplated that the sample can be in the gas phase (solution) or liquid phase and detecting of the co-location can be conduct also in solution or in air.

In certain embodiments, methods of detecting and isolating a sample or samples are disclosed. One method comprises the steps of contacting a colored nanostructure having an analyte-binding member with a sample in a solution, dispersing the solution on a magnetic grid, observing or evaluating the co-location of the colored nanostructure and the sample, wherein the co-location indicates the nature of the sample. The method further comprises a step of isolating the observed sample. Observation can be conducted through optical means such as microscope. The other method comprises the steps of contacting mixing a first colored nanostructure having a first analyte-binding member, a second colored nanostructure having a second analyte-binding member, and a plurality of samples in a mixture, dispersing the mixture on a magnetic grid, observing or evaluating the co-location of 1) the first colored nanostructure and the first sample, and/or 2) the second colored nanostructure and the second sample, wherein the co-location indicates the nature of the first sample or the second sample. The method further comprises a step of isolating the observed first or second sample.

Figure 2A:
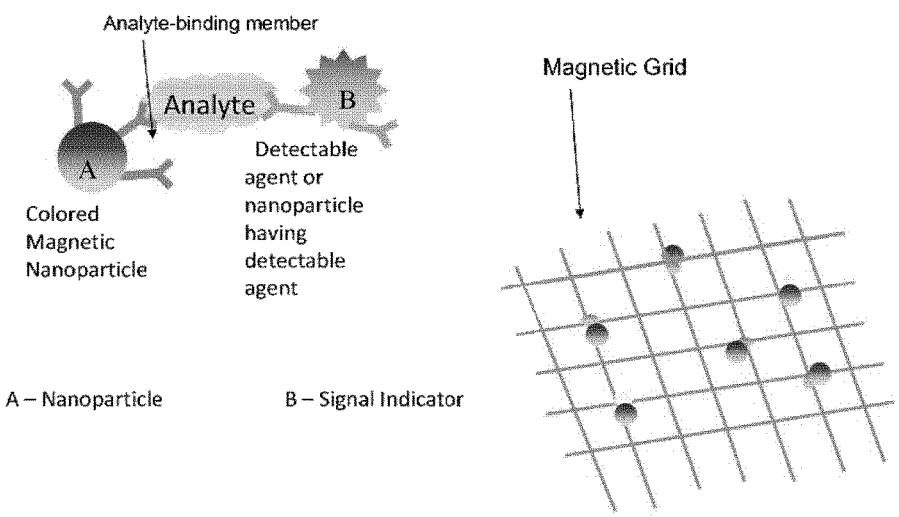
FIG. 2(A)-2(B) are schematic drawings of methods for analyte detection with a signal indicator.

Another aspect of the present disclosure relates to a magnetic nanostructure complex comprising a magnetic nanostructure (colored or non-colored) having an analyte-binding member, an analyte which specifically binds to the analyte-binding member or is specifically captured by the member, and a signal indicator. As shown in FIG. 2(A), the magnetic nanostructure (colored or non-colored) captures the analyte through the analyte-binding member and the captured analyte is bounded to a signal indicator. The signal indicator contains an analyte-binding member capable of binding to the captured analyte (e.g., an antibody to the captured analyte) and a detectable signal. The detectable signal is operably linked to or conjugated to the analyte binding member of the signal indicator. For example, the detectable signal can be any detectable agents disclosed herein or a non-magnetic nanoparticle detectable by detectable agents associated therein or bar-coding. For instance, the signal indicator can be an antibody conjugated to a detectable agent or a non-magnetic nanoparticle having an analyte-binding member and a detectable agent. In certain embodiments, the second analyte binding member binds to a different region, part, and epitope from that of the first analyte binding member. It is contemplated that the non-magnetic nanoparticle includes but is not limited to the nanoparticle that has been disclosed in U.S. Prov. Appl. 61/589,777 and U.S. patent application Ser. No. 12/460,007, as far as the non-magnetic nanoparticle is capable of carrying the analyte-binding member and releasing a color signal through the detectable agent associated therewith or bar-coding (QDs) therewithin.

Another aspect of the present disclosure relates to a system which is disclosed herein to having a magnetic nanostructure (colored or non-colored) and a substrate having a magnetic grid, wherein the nanostructure is dispersed onto the magnetic grid. The system further comprises an analyte that specifically binds to the analyte-binding member of the nanostructure. The system further comprises a signal indicator (as shown in FIG. 2(A)).

Figure 2B:
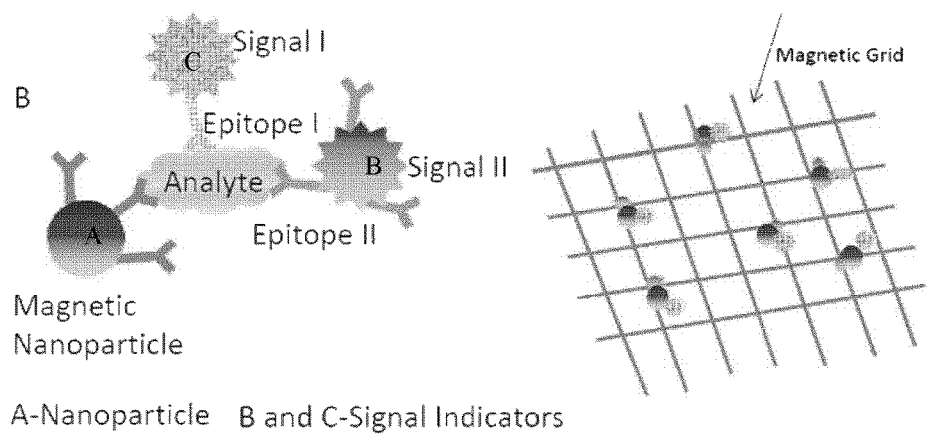

In certain embodiment, a system disclosed herein comprises a plurality of signal indicators that bind to the same analyte (e.g., via different regions, parts, epitopes of the analyte that the analyte-binding member of the nanoparticle binds to). As shown in FIG. 2(B), an analyte is bounded or captured by a magnetic nanostructure via the analyte binding member of the magnetic nanostructure. A first signal indicator comprises a first analyte binding member (binding to the captured analyte) and a first detectable signal. A second signal indicator comprises a second analyte-binding member (binding to the captured analyte) and a second detectable signal. The first and second detectable signals can be same. The first binding member may be different from the second binding member (e.g., the first binds to different regions or parts or epitopes of the captured analyte), yet both bind to the captured analytes in different regions, parts or epitopes from the analyte-binding member of the magnetic nanostructure. The presence and/or the quantity of the analyte can be further detected and enhanced through the first and second signal indicators.

Figure 3A:
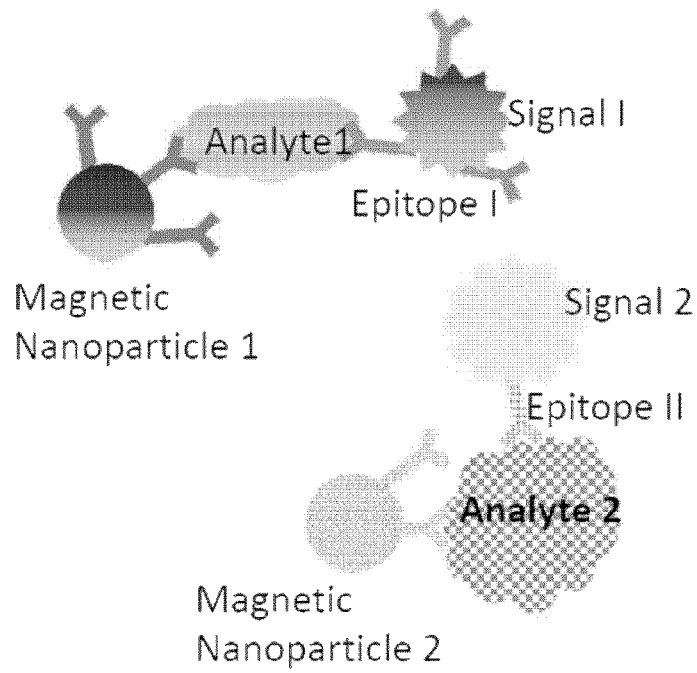
FIG. 3(A)-3(C) are schematic drawings of methods for detection of more than one analyte with signal indicators.
Figure 3B:
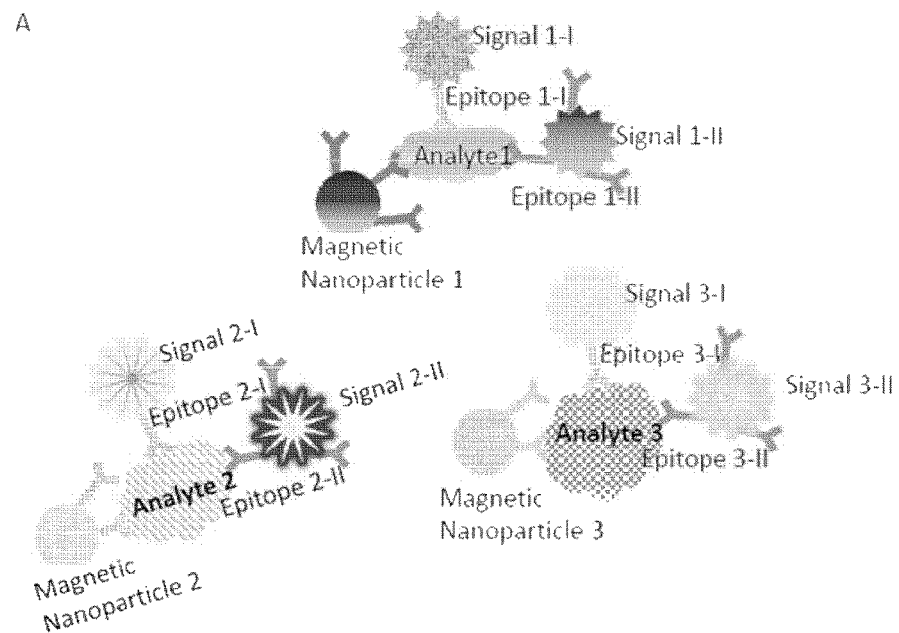

Another aspect of the present disclosure relates to a multiplex system comprising substrate having a magnetic grid and a first magnetic particle (colored or non-colored) and a second magnetic particle (colored or non-colored). As shown in FIG. 3(A), the first magnetic nanostructure is operably associated with a first analyte binding member capable of binding to or capturing a first analyte, and the second magnetic nanostructure is operably associated with a second analyte binding member capable of binding to or capturing a second analyte. The multiplex system further comprises a first signal indicator (capable of binding to the first analyte and indicating the presence or quantity of the first analyte via a first detectable signal) and a second indicator (capable of binding to the second analyte and indicating the presence or quantity of the second analyte via a second detectable signal). As shown in FIG. 3(B), the multiplex system further comprise a plurality of first signal indicators (or a group of first signal indicators that are capable of binding to the first analyte) and a plurality of second signal indicators (or a group of second signal indicators that are capable of binding to the second analyte).

Figure 3C:
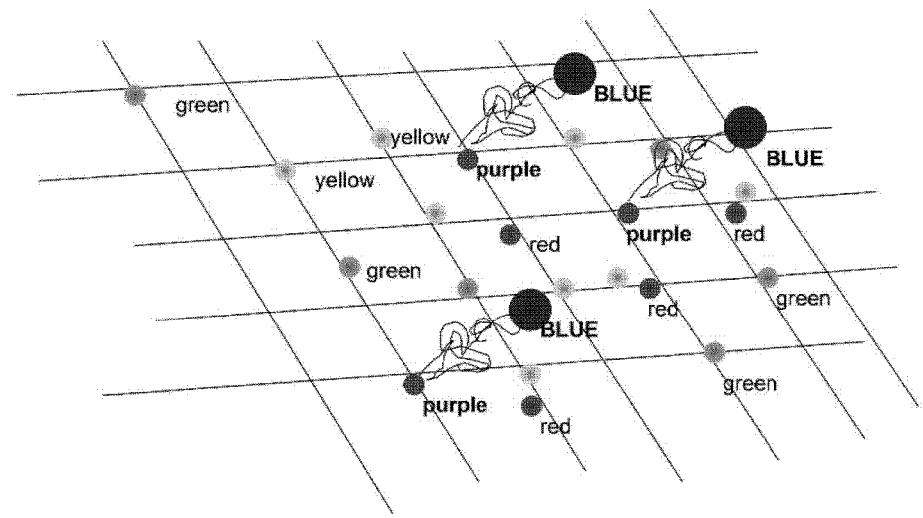

In certain embodiments, methods of using the colored magnetic nanostructure complex are disclosed. As shown in FIG. 3(C), the method comprises the steps of forming a nanostructure complex, and dispersing the nanostructure complex onto a substrate having a magnetic grid. For another example, the method comprise the steps of dispersing a colored magnetic nanostructure onto the substrate having a magnetic grid, contacting a sample (the sample may or may not have an analyte) with the nanostructure having an analyte-binding member; and then contacting a signal indicator with the mixture; wherein the presence (and/or intensity) of signal indicates the presence (and/or the quantity) of the analyte in the sample. For another example, the method comprises the steps of mixing the magnetic nanostructure, the sample, and the signal indicator together first and then dispersing the mixture onto a magnetic grid on s substrate or in a container. After the disbursement, the substrate or the container can be washed or processed to remove noise signals or non-binding factors.

In certain embodiments, a multiplex composition having a plurality of colored magnetic nanostructure complexes are disclosed. As show in FIG. 3(C), the multiplex composition comprises a first colored magnetic nanostructure and a second colored magnetic nanostructure (the first and second nanostructures have different bar-codes or colors and carries different analyte-binding members). The complex further comprises a substrate having a magnetic grid where the nanostructures are dispersed onto the grid. The complex further comprise a first analyte or a second analyte that binds to the first or the second nanostructure respectively; and a first signal indicator or a second signal indicator, both indicators binds to the first and second analytes respectively. As a result, various analytes (e.g., protein, DNA, carbohydrates, lipid, and cell) in a sample or a mixture can be detected and quantified at the same time in the same substrate.

In certain embodiments, methods of detecting analytes are disclosed using a plurality of magnetic nanoparticles (colored or non-colored). As shown in FIGS. 3(A), (B) & (C), one example of methods comprise the steps of dispersing a first magnetic nanostructure and a second magnetic nanostructure onto a substrate having a magnetic grid; contacting a sample with the substrate, wherein the sample may or may not have a first analyte or a second analyte; contacting a first signal indicator (or a plurality of first signal indicators) and a second signal indicator (or a plurality of second signal indicators) with the substrate; the presence of the first analyte and/or the second analyte in the sample is indicated by the signal (e.g., color or detectable signal) of the first and/or second signal indicator. Another example of methods comprises forming a plurality of colored magnetic nanostructure complexes first (or mixing the plurality of magnetic nanostructures (e.g., a first magnetic nanoparticle and a second magnetic nanoparticle), a sample and a plurality of signal indicators (e.g., a first signal indicator or first signal indicators and a second signal indicator or second signal indicators) and dispersing the mixture onto a substrate having magnetic grid. It is contemplated that the sample, the contacting, and detecting can be conducted either in the solution or in air, depending on the phase of sample.

Figure 4:
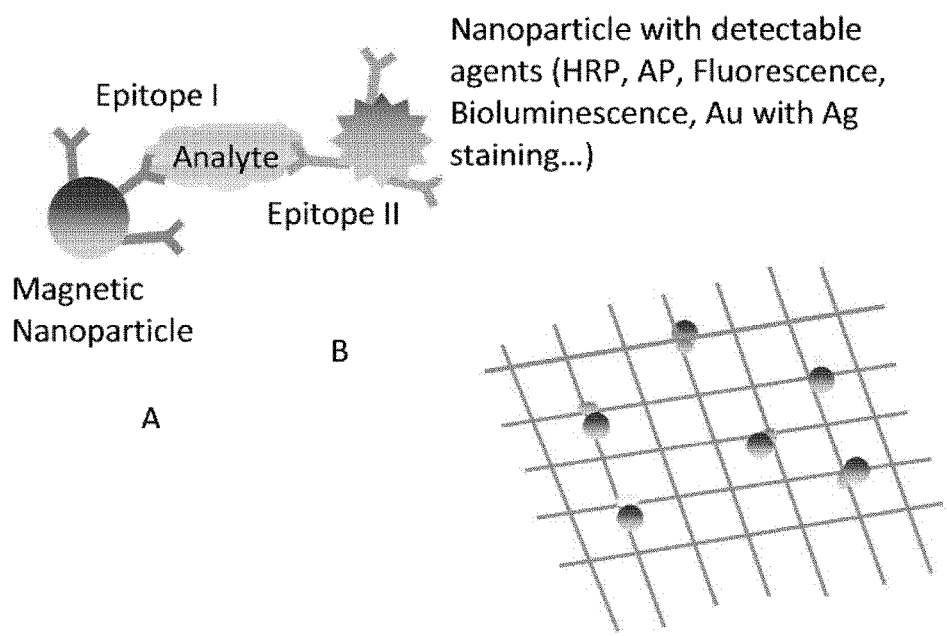
FIG. 4 is a schematic drawing of the detection step. Magnetic grid will be applied at step A to capture the magnetic nanostructures, or magnetic nanostructure with analyte attached, then the signal generating step B happens on the 2D magnetic grid surface. Alternatively, the grid step can also be applied after solution reaction of both step A and B, for fluorescence based detection similar to FIG. 2.

In certain embodiments, as shown in FIG. 4, a magnetic nanostructure (with or without color) has a first analyte-binding member (e.g., a first antibody) that binds specifically a first epitope of an analyte (e.g., a protein); a signal indicator (e.g., a non-magnetic nanostructure carrying detectable agents) has a second analyte-binding member (e.g., a second antibody) that binds to a second epitope of the analyte, wherein both epitopes do not substantially overlap with each other. The nanostructure complex (or complexes) formed herein can be dispersed on a substrate having a magnetic grid. The signals (and/or strength) from the detectable agents indicates the presence (and/or quantity) of the analyte. It is contemplated that a plurality of different magnetic nanostructures can be used to detect and quantify a plurality of different analytes in a sample.

Figure 5:
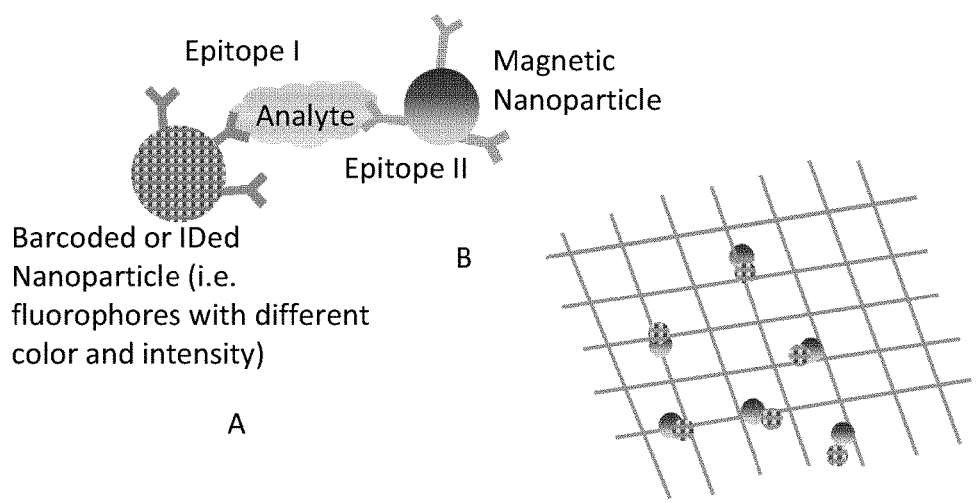
FIG. 5 is a schematic drawing of the detection method using a barcoded or IDed nanostructure. Both steps A and B could proceed as solution reaction, then the magnetic grid could be applied. Presence or capture of barcode on the grid indicates presence of analyte in solution.

In certain embodiments, as shown in FIG. 5, a nano-complex comprises a colored nanostructure without magnetic feature (non-magnetic colored nanostructure) is operably linked with a first analyte-binding member, whereas the first member (a first antibody or fragment thereof) specifically binds to a first epitope of an analyte (e.g., an antigen). The nano-complex further comprises an analyte that binds to the first analyte-binding member. The nano-complex further comprises a magnetic nanostructure being operably linked to a second analyte-binding member that binds to a second epitope of the same analyte. It is contemplated that the non-magnetic colored nanostructure include but are not limited to the nanostructure that has been disclosed in U.S. Prov. Appl. 61/589,777 and U.S. patent application Ser. No. 12/460,007, as far as the non-magnetic nanostructure is capable of carrying an analyte-binding member and releasing a color signal via its own bar-coding or a detectable agent associated therewith. It is further contemplated that the magnetic nanostructure include but are not limited to the nanostructure that has been disclosed in U.S. Prov. Appl. 61/589,777 and U.S. patent application Ser. No. 12/460,007, as far as the magnetic nanostructure is capable of carrying an analyte-binding member.

In certain embodiment, a method of detecting an analyte using a nano-complex is disclosed. For example, the method comprises the steps of contacting a colored nanostructure having a first analyte-binding member with a sample (to be detected that may or may not have the analyte to be detected) in a mixture; contacting a magnetic nanostructure having a second analyte-binding member with the mixture; dispersing the mixture in a substrate having a magnetic grid, and detecting the color of the colored nanostructure, wherein the presence and/or intensity of the color indicate the presence and quantity of the analyte in the sample. It is contemplated that a plurality of different colored nanostructures can be used to detect and quantify a plurality of different analytes in a sample.

It is contemplated in the present disclosure that bar-coded or colored nanostructure(s) or nanostructure complex(es) or signal indicators disclosed herein can be detected in solution without the needs for array or substrate in real time. For example, as disclosed in U.S. Pat. No. 796,392, light sources passing through the solution containing a plurality of IDed nanostructure and the value of passing through light is detected by photosensors. Light data is then collected through an imaging arrangement and processed to facilitate focusing and optical correction via software. As a result, the information about the nanostructures or complexes are recoded by passing the light through once without the need for focusing image on each focal plane. The same image computation is also used in microscope. Under the microscopic setting, the solution is imaged by passing light from a microlens array to a photosensor array to simultaneously detect light from the solution which is passed through different directions to different locations. The light data is then analyzed to gain datasets for all IDed nanostructures in the solution in the single shot (For detailed information, see U.S. Pat. No. 7,723,662).

Additionally, the magnetic grid can be commercially available. For example, Industry Netting provides electroformed screens that can be used as magnetic grid (http://www.industrialnetting.com/metal_electro.htm). Microfabricated magnetic sifter can be made as magnetic substrate with grids (See Earhartt at el., Journal of Magnetism and Magnetic Materials 321: 1436-1439 (2009).

Figure 6:
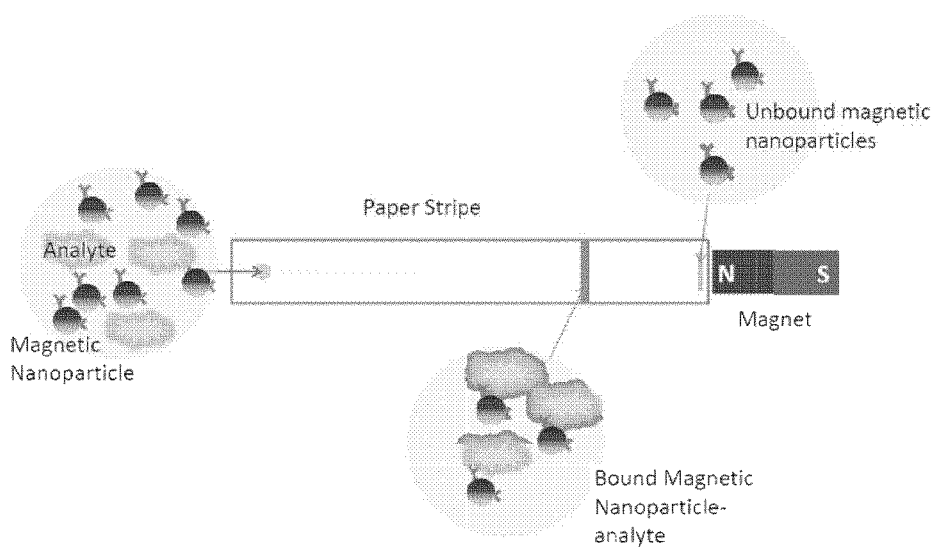
FIG. 6 is a schematic drawing of a detection method based on lateral flow assay. Analyte detection in a paper strip testing using the magnetic nanoparticles and signal generating scheme. An analyte sample could be mixed with the magnetic nanoparticles in solution. The analyte is bounded or captured by a magnetic nanoparticle via the analyte binding member of the magnetic nanoparticle. The solution is applied onto the paper strip and flow along the paper strip. When it is passing through the pre-defined position of an analyte capturing region which could be pre-deposited with analyte binding members, the analyte bound magnetic nanoparticles are captured at the pre-defined position, the signal/color, for example, fluorescence of the magnetic nanoparticle could be used to identify the existence of the analyte. A magnetic field gradient is applied to attract unbound magnetic nanoparticles away from the pre-defined position for analyte identification. This could remove the background signal and increase signal to noise ratio hence detection sensitivity of a paper strip testing assay. Both antibody-antigen and nucleic acid interaction could be utilized in such scheme.

In certain embodiment, the magnetic nanoparticles (colored or not colored) can also interact with the analyte through a solid media, such as a lateral flow immunoassay in a test strip (e.g. a porous paper or a sintered polymer). For example, a first analyte binding member or members can be pre-deposited or immobilized in a specific position of the test strip. A sample (to be tested for an analyte) and the magnetic nanoparticle having a second analyte binding member are mixed in a solution and applied to the test strip. When the analyte is present in the sample, the magnetic nanoparticle will bind to the position of the first analyte binding member. If the magnetic nanoparticle in the solution is colored for example by fluorescence or IDed, then the signal can be detected to indicate the presence of the analyte and/or the quantity of the analyte. The magnetic nanoparticle may not need a color but using additional signal generating mechanism, for example, in the nucleic acid interaction scenario, the presence of nucleic acid and their interaction could be indicated through the staining of a double strand nucleic acid, or by changes reflecting enzymatic interactions involving the analyte. The magnetic properties of the particle will allow the application of a magnetic field gradient at the end position of the test strip, for example, by physically positioning a permanent magnet, or on the top of the test strip, to remove the un-bound magnetic nanoparticles away from the test strip, hence to reduce background signal of non-specific or false positive binding. This is a distinct feature not existing in all other paper testing strip assays. The application scheme is illustrated in FIG. 6.

In certain embodiments, the methods provided herein further comprise separating the analyte from the sample. For example, the magnetically captured analyte can be separated from the sample using a magnetic grid. The separated analyte may optionally be quantified or further analyzed. The separated analyte may also be redispersed in a suitable washing or eluting solution.

Methods for Preparing the Composition

Another aspect of the present disclosure relates to methods of forming a composition comprising a nanostructure operably linked to an analyte-binding member.

In certain embodiments, the analyte-binding members and/or the detectable agent may be mixed with a readily formed nanostructure, e.g., in solution, dispersion, suspension, emulsion etc, to allow incorporation of the analyte-binding members to the porous compartment of the nanostructure, or to allow conjugation of the analyte-binding members to the functional groups on the nanostructure.

In certain embodiments, the analyte-binding members and/or the detectable agent may be introduced during or after the formation of the nanostructures. For example, when the nanostructure is formed through silanization process, the analyte-binding members can be introduced to the silanization system, so as to allow the incorporation of the analyte-binding member into the nanostructure during the silanization process. For another example, for a nanostructure having a surface reactive group (such as streptavidin), the analyte-binding member comprises a binding partner to the reactive group (such as biotin) can be mixed with the nanostructure under conditions which facilitate the binding.

Methods for Preparing the Nanostructure

Another aspect of the present disclosure relates to methods of forming a nanostructure comprising at least one core nanoparticle with a coating. For example, the nanostructure is formed by coating or surrounding one or more core nanoparticle with a coating material such that the particle(s) is or are embedded in the coating material. For another example, the coating material is formed by crosslinking a precursor in the presence of a core nanoparticle, so that the nanoparticle is embedded in the crosslinked coating material.

In certain embodiments, the method further comprises introducing one or more functional groups within or on the surface of the nanostructure. The functional groups may be introduced during the formation of the coating material. For example, during the cross-linking process, precursors containing such functional groups can be added, in particular, during the ending stage of the cross-linking process. The functional groups may also be introduced after the formation of the nanostructure, for example, by introducing functional groups to the surface of the nanostructure by chemical modification. In certain embodiments, the functional groups are inherent in the nanostructure or in the coating material.

The functional groups serve as linkage between the nanostructure and the analyte binding member. Examples of the functional groups include, but are not limited to amino, mercapto, carboxyl, phosphonate, biotin, streptavidin, avidin, hydroxyl, alkyl or other hydrophobic molecules, polyethylene glycol or other hydrophilic molecules, and photo cleavable, thermo cleavable or pH responsive linkers.

In certain embodiments, the method further comprises purifying the obtained nanostructure product. The purification may include use of dialysis, tangential flow filtration, diafiltration, or combinations thereof.

Methods for Preparing the Nanostructure Having a Low-Density Porous 3-D Structure Another aspect of the present disclosure relates to methods of forming a nanostructure comprising at least one core nanoparticle with low-density, porous 3-D structure. For example, the nanostructure is formed by coating or surrounding one or more core nanoparticle with low density, porous 3-D structure such that the particle(s) is or are embedded in the 3-D structure.

The low-density, porous 3-D structure is formed by the depositing, or covering of the surface of the core nanoparticle through the assembly or cross-linking of silane-containing or silane-like molecules. The low density porous 3-D structure can be prepared by a silanization process on the surface of the core nanoparticles. Silanization process includes, for example, the steps of crosslinking silicon-containing or silane-like molecules (e.g., alkoxysilanes such as amino-propyl-trimethoxysilane, mercapto-propyl-trimethoxysilane, or sodium silicate) under acidic or basic conditions.

In certain embodiments, an acidic or a basic catalyst is used in the crosslinking Exemplary acid catalyst include, without limitation, a protonic acid catalyst (e.g., nitric acid, acetic acid and sulphonic acids) and Lewis acid catalyst (e.g., boron trifluoride, boron trifluoride monoethylamine complex, boron trifluoride methanol complex, $FeCl_3$, $AlCl_3$, $ZnCl_2$, and $ZnBr_2$). Exemplary basic catalysts include, an amine or a quaternary ammonium compound such as tetramethyl ammonium hydroxide and ammonia hydroxide.

The silanization process may include one or more stages, for example, a priming stage in which the 3-D structure starts to form, a growth stage in which a layer of siliceous structure is readily formed on the core nanoparticle and more are to be formed, and/or an ending stage in which the 3-D structure is about to be completed (e.g., the outer surface of the 3-D structure is about to be formed). During the silanization process, one or more silane-containing molecules can be added at different stages of the process. For example, in the priming stage, organosilanes such as amino-propyl trimethoxyl silane or mercaptopropyl trimethoxyl silane can be added to initiate the silanization on the core nanoparticle surface. For another example, silane molecules having fewer alkoxy groups (e.g., only 2 alkoxy groups) can be added to the reaction at the growth stage of silanization. For another example, at the ending stage of silanization, organo silane molecules with one or a variety of different functional groups may be added. These functional groups can be amino, carboxyl, mercapto, or phosphonate group, which can be further conjugated with other molecules, e.g., hydrophilic agent, a biologically active agent, a detectable label, an optical responsive group, electronic responsive group, magnetic responsive group, enzymatic responsive group or pH responsive group, or a binding partner, so as to allow further modification of the 3-D structure in terms of stability, solubility, biological compatibility, capability of being further conjugation or derivation, or affinity to payload. Alternatively, the functional groups can also be a group readily conjugated with other molecules (e.g., a group conjugated with biologically active agent, a thermal responsive molecule, an optical responsive molecule, an electronic responsive molecule, a magnetic responsive molecule, a pH responsive molecule, an enzymatic responsive molecule, a detectable label, or a binding partner such as biotin or avidin).

To control the formation of low density siliceous structure, the preparation further includes density reducing procedures such as introducing air bubbles in the reaction or formation, increasing reaction temperature, microwaving, sonicating, vertexing, labquakering, and/or adjusting the chemical composition of the reaction to adjust the degree of the crosslinking of the silane molecules. Without being bound to theory, it is believed that these procedures can help make the reaction medium homogeneous, well dispersed and promote the formation of low density porous 3-D structure with increased voids or porosity.

In certain embodiments, the density reducing procedure comprises sonicating the reaction or formation mixture. The conditions of the sonicating procedure (e.g., duration) in the silanization process can be properly selected to produce a desired porosity in the resulting low density porous 3-D structure. For example, the sonicating can be applied throughout a certain stage of the silanization process. The duration of sonicating in a silanization stage may last for, e.g., at least 1 hour, 1.5 hours, 2 hours, 2.5 hours, 3 hours, 3.5 hours, 4 hours. In certain embodiments, sonicating is applied in each stage of the silanization process.

In certain embodiments, the density reducing procedures comprise introducing at least one alcohol to the reaction. In certain embodiments, the alcohol has at least 3 (e.g., at least 4, at least 5 or at least 6) carbon atoms. For example, the alcohol may have 3, 4, 5, 6, 7, 8, 9, 10, 11, 12 or more carbon atoms. In certain embodiments, the alcohol can be monohydric alcohols, or polyhydric alcohols. Illustrative examples of monohydric alcohols include, propanol, butanol, pentanol, hexyl alcohol, etc. Illustrative examples of polyhydric alcohols include, propylene glycol, glycerol, threitol, xylitol, etc. In certain embodiments, the alcohol can have a saturated carbon chain or an unsaturated carbon chain. An alcohol having a saturated carbon chain can be represented as $C_nH_{(2n+2)}O$ in chemical formula. In certain embodiments, n is no less than 3, or no less than 4, or no less than 5 (e.g., n=3, 4, 5, 6, 7, 8, 9, 10, 11, 12 or more). Alcohol with an unsaturated carbon chain has a double or a triple bond between two carbon atoms. In certain embodiments, the alcohol can be a cyclic alcohol, for example, cyclohexanol, inositol, or menthol.

In certain embodiments, the alcohol can have a straight carbon chain (e.g., n-propyl alcohol, n-butyl alcohol, n-pentyl alcohol, n-hexyl alcohol, etc) or a branched carbon chain (e.g., isopropyl alcohol, isobutyl alcohol, tert-butyl alcohol, etc). In certain embodiments, the alcohol is present in a volume fraction of about 30% to about 70% (e.g., about 30% to about 70%, about 30% to about 60%, about 30% to about 55%, about 40% to about 70%, about 45% to about 70%, about 40% to about 60%). In certain embodiments, the alcohol is present in volume fraction of around 50% (e.g., around 45%, around 46%, around 47%, around 48%, around 49%, around 50%, around 51%, around 52%, around 53%, around 54%, around 55%, around 56%, around 57%, around 58%, around 59%, or around 60%,).

In certain embodiments, the density reducing procedure comprises introducing air bubbles to the reaction. In certain embodiments, the air bubbles can be in constant presence during the reaction process. The air bubbles can be introduced to the reaction through any suitable methods, for example, by blowing bubbles to the reaction, or by introducing a gas-producing agent to the reaction mixture.

Other experimental conditions can also be optimized to provide for formation of a desired low density porous 3-D structure. Such experimental conditions include, for example, the concentration of the core nanoparticles, the concentration of the catalyst, the ratio of the concentration of the catalyst to the core nanoparticle, the temperature at which the low density siliceous structure is formed, or the molecular structure of the organosilanes.

The thickness of the low density porous 3-D structure, which directly correlates to the size of the nanostructure, could be controlled (e.g., from 1 nm to 1000 nm) by, for example, modifying the quantity of the silane-containing molecules (e.g., trialkoxysilane or sodium silicate), the reaction time, and time lapse between reaction steps and such kind of reaction parameters.

The thickness of the 3-D structure can be about 1 to 5 nm thick. In certain embodiments, the thickness can be about 1 to 10 nm thick. In certain embodiments, the thickness can be about 1 to 20 nm thick. In certain embodiments, the thickness can be about 1 to 30 nm thick. In certain embodiments, the thickness can be about 1 to 40 nm thick. In certain embodiments, the thickness can be about 1 to 50 nm thick. In certain embodiments, the thickness can be about 1 to 60 nm thick. In certain embodiments, the thickness can be about 1 to 100 nm thick. In certain embodiments, the thickness can be about 1 to 500 nm thick. In certain embodiments, the thickness can be about 1 to 1000 nm thick.

After the low-density, porous 3-D structure is formed on the surface of the core nanoparticle, the core nanoparticle is embedded in the 3-D structure. The resulting nanostructure can have a thickness (e.g., the longest dimension of the nanostructure or a diameter if the structure is a sphere) of about 1 to 1000 nm, 1 to 100 nm, or 1 to 10 nm. In another embodiment, the nanostructure can have a diameter of about 1 to 30 nm. In another embodiment, the nanostructure can have a diameter of about 500 nm. In another embodiment, the nanostructure can have a diameter of about 100 nm. In another embodiment, the nanostructure can have a diameter of about 50 nm. In another embodiment, the nanostructure can have a diameter of about 30 nm. In another embodiment, the nanostructure can have a diameter of about 10 nm.

Products by Process

Another aspect of the present disclosure relates to composition prepared by any of the methods provided herein. The composition prepared herein may be operably linked with one or more analyte-binding members, using methods described herein and/or conventional methods known in the art. In certain embodiments, the composition prepared in the present disclosure can be further characterized for the low density porous 3-D structure, such as density, porosity, surface areas, thickness etc. of the 3-D structure. Optionally, the analyte-binding members may be characterized as well, such as the amount of the analyte-binding member or the detectable signal of the analyte-binding member.

EXAMPLES

Figure 10:
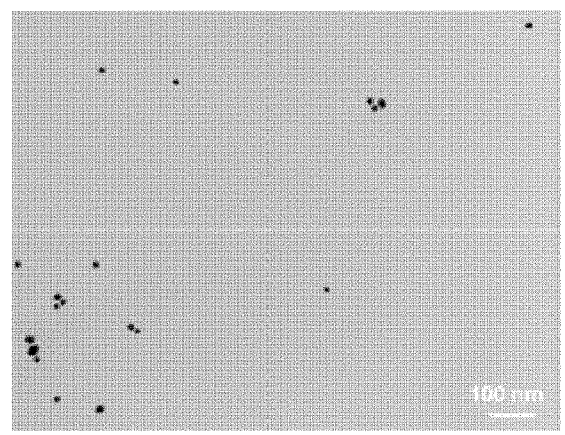
FIG. 10 shows an exemplary TEM image of silanized Au nanoparticles with core size of Au at ~20 nm and hydrodynamic size ~60 nm. No siliceous coating is visible from the TEM.

Example 1. Preparation of Nanoparticles of Gold and Semiconductor Quantum Dots with the Low Density Siliceous Structure The low density siliceous structure is a versatile and flexible platform for making biocompatible nanoparticles. For example, to incorporate gold nanoparticles into the siliceous structure, Au nanoparticles synthesized in either water solution or organic solutions could be utilized. Briefly, Au was precipitated out at the sample vial bottom after centrifuge at 13 k rpm for 15 min, then silane molecules such as aminopropyltrimethoxysilane and TMAOH was added. The reaction solvent was adjusted using a higher number alcohol, such as butanol or proponol. Then the sample was sonicated for a few hours with constant blowing of air bubbles, afterwards, PEG-silane, mercaptopropyltrimethoxysilane and aminopropyltrimethoxysilane were added, the sample was sonicated for additional 2-3 hours. Afterwards, mixture of chlorotrimethylsilane, methanol, and TMAOH or other silane molecules that only have one alkoxyl group connecting with the silicon atom were added to react with surface siloxyl groups presented on the surface of the already grown siliceous structure. After additional sonicating and aging, stable nanoparticles with the highly porous siliceous structure were collected and stored within physiological buffer solutions through centrifugal filtering, centrifugation, dialysis or any other solution exchange methods. The resulting Au nanostructure was observed under TEM, and an exemplary TEM image was shown in FIG. 10. The nanoparticle core size was about 20 nm and hydrodynamic size was about 60 nm. The siliceous coating was not obvious from the TEM.

Figure 11:
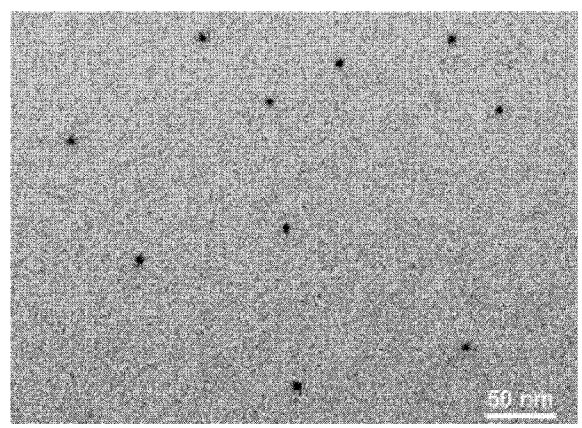
FIG. 11 shows an exemplary TEM image of silanized quantum dots with nanoparticle core size of ~6 nm and hydrodynamic size ~200 nm. The siliceous coating is not obviously visible from the TEM.

Example 2. Preparation of Nanoparticles of Semiconductor Quantum Dots with the Low Density Siliceous Structure As another example, semiconductor quantum dots in the form of individual nanocrystal or nanocrystal clusters could also be incorporated within the highly porous/low density siliceous structure. For example, CdSe/ZnS nanoparticles in organic solvents such as chloroform, Toluene, or Hexane could be precipitated out by adding methanol and then through centrifugation. The nanocrystal pellet was then re-dispersed in aminopropyltrimethoxysilane or mercaptopropyltrimethoxysilane. Afterwards, tetramethyl ammonium hydroxide was added. Then the reaction solvent was adjusted using a higher number alcohol, such as butanol or proponol. After sonicating the sample for 1-4 hours and blowing air bubbles, small amount of aminopropyltrimethoxysilane, mercaptopropyltrimethoxysilane, polyethyleneoxidesilane and water was subsequently added, and the sample then underwent sonication for another 1 to 4 hours. Then, mixture of chlorotrimethylsilane, methanol, and TMAOH or other silane molecules that only have one alkoxyl group connecting with the silicon atom were added. This sample was then sonicated for another 1-4 hours, followed by overnight aging under mild shaking or vibration. The resulting nanoparticles with low density/highly porous siliceous structure were transferred into physiological buffer solutions by centrifugal filtering, centrifugation, dialysis or any other solution exchange methods. The resulting CdSe/ZnS nanostructure was observed under TEM, and an exemplary TEM image was shown in FIG. 11. The nanoparticle core size was about 10 nm and hydrodynamic size was about 200 nm. The siliceous coating was not obvious from the TEM.

Example 3. Preparation and Characterization of Low Density Magnetic Particles

Figure 12:
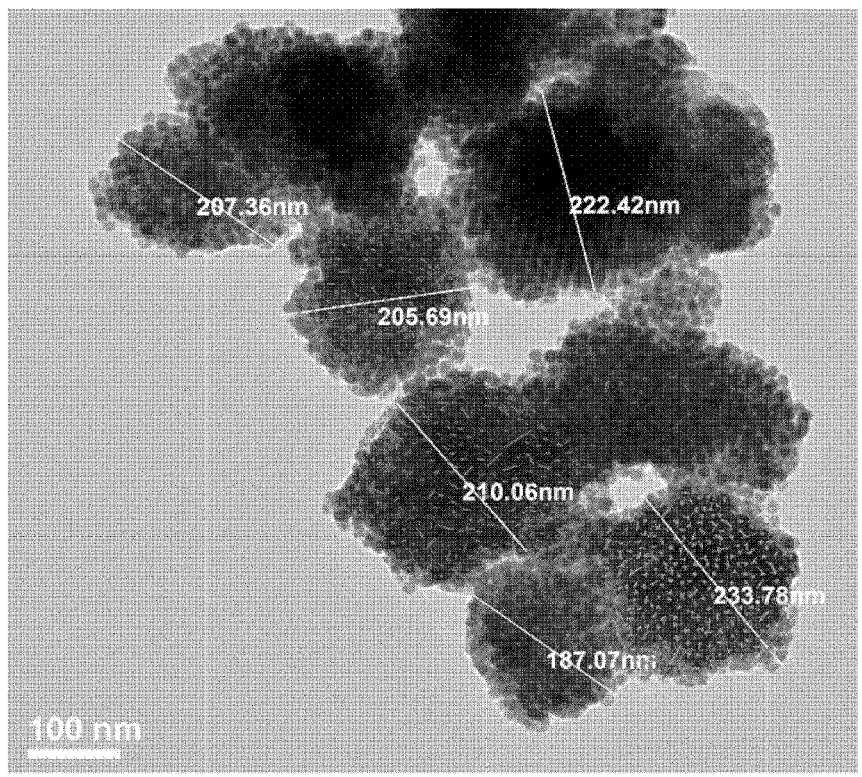
FIG. 12 shows an exemplary TEM image of porous nanostructure, in which the diameters of the large core nanoparticles are shown.

Preparation of the Magnetic Porous Nanostructure:

Magnetic particles formed by clustering multiple small particles and then being coated were prepared. The clustering happened with the addition of a worse solvent for generating dispersed nanoparticles, such as butanol or isopropanol, followed by the addition of the silanization reagents to form the nanostructure under constant blowing of air bubbles. The magnetic nanostructure as prepared was observed under TEM (FIG. 12). As shown in FIG. 12, each large core nanoparticle comprised a cluster of small nanoparticles, and the coating was substantially invisible under TEM.

Characterization of Density of the Coating:

To calculate the density of the coating, both the dry mass and the volume of the coating were characterized.

Since the magnetic particles had high magnetic response that they could be directly captured using a magnet. This allowed generation of dry particles to measure the mass of the material. The dry mass of particles before and after coating was quantified as follows. 200 ul of the coated particle solution was pipetted out into a centrifugal vial whose mass was pre-measured. Coated magnetic nanoparticles were captured to the side of the vial wall, and the supernatant was removed. The captured particles were washed with water. At the end, the particles absorbed to the side wall were left to dry in the open vial under a fume hood. The mass of the vial with the dry coated particles were measured. The dry coated particle mass was calculated by subtraction of the mass of the vial from the mass of the vial with the dry coated particles inside. To measure the mass of the particles before coating, uncoated particles corresponding to the same amount of the magnetic material as in the coated nanoparticles, assuming an 80% coating processing yield, was captured to the side of the vial, and dried. The dry mass of the particles before coating was measured by subtraction of the mass of the vial from the mass of the vial with the dry uncoated particles inside. The mass of the coating was equal to the mass of the dry coated particles minus the dry mass of particles before coating.

TABLE 1

| Average Core mass (n = 3) | 0.67 mg |
| Average Coating mass (n = 3) | 0.06 mg |

The total volume of the coating was calculated using the number of large particles in the above mass multiplied by the volume of the coating of each individual large nanoparticles. The particles were suspended in an aqueous solution, and the volume of the coating of each large particle was calculated as $4/3 \times \pi (R^3_{with\ coating} - R^3_{core})$, in which the $R_{with\ coating}$ of an individual large nanoparticle was measured using dynamic light scattering (DLS) technique, and the $R_{core}$ of the large core particle was directly imaged and measured using TEM (see FIG. 12).

TABLE 2

| Average size of large core nanoparticles under TEM | 210 nm |
| Average size of coated large nanoparticles under DLS | 217-357 nm |
| Average coating volume of an coated large nanoparticle | $4/3 \times \pi (110^3 - 105^3)$ nm$^3$ |

The number of large particles in the mass was calculated by dividing the total number of small nanoparticles by the number of small nanoparticles in each large nanoparticle. The total number of small nanoparticles was estimated by dividing the mass of total magnetic material by the mass of an individual small nanoparticle (i.e. calculated using the size and density of the small nanoparticle). The number of small nanoparticles in each individual large particle was counted from the TEM micrograph. Hence, the total volume of the coating can be calculated as the volume of coating of a large nanoparticle multiplied by the total number of the large nanoparticles.

TABLE 3

| Core mass | 0.67 mg |
| --- | --- |
| Density of core | 5.2 kg/m$^3$ |
| Small nanoparticle size | 16 nm |
| Small nanoparticle Volume | 2.1 × 10$^{-24}$ m$^3$ |
| Mass of each small nanoparticle | 1.1 × 10$^{-17}$ mg |
| Number of small particles in the core | 6.1 × 10$^{16}$ |
| Average number of small particle per large particle | 236 |
| Number of large particles in the core | 2.6 × 10$^{14}$ |
| Total volume of the coating | 4/3 × π (110$^3$ − 105$^3$) nm$^3$ × 2.6 × 10$^{14}$ = 0.1875 × 10$^{-6}$ m$^3$. |

The density of the coating was calculated using the mass of the coating divided by the total volume of the coating, i.e., 0.06 mg/0.1875×10$^{-6}$ m$^3$=0.32 mg/cm$^3$.

The density of the low density siliceous structure prepared herein is only 0.32 mg/cm$^3$, which is significantly lower than the density of some reported silica coatings, for example, those reported in Vincent et al (Vincent, A. et al, J. Phys. Chem. C 2007, 111, 8291-8298), that have a density of 1-2 g/cc and are 10$^4$ denser than the siliceous structure provided herein.

Characterization of Porosity Using BET Method:

Large magnetic nanoparticles after coating were captured to the side of the vial and dried. 2 samples of 65 mg (sample 1) and 45 mg (sample 2) dry mass were prepared for the BET measurement.

Surface pore sizes were measured using BET method for the dry mass of the coated nanoparticles. The results are shown in the below Tables.

TABLE 4

| Characterization for Sample 1 | |
| --- | --- |
| Surface Area | 14.166 m$^2$/g |
| Total pore volume for pores smaller than 677.5 Å (Radius) at P/P$_0$ = 0.98562 | 7.562 × 10$^{-2}$ cc/g |

TABLE 5

| Characterization for Sample 2 | |
| --- | --- |
| Surface Area | 6.380 m$^2$/g |
| Total pore volume for pores smaller than 683.3 Å (Radius) at P/Po = 0.98575 | 7.099 × 10$^{-2}$ cc/g |

The surface area and the pore volume of the porous nanostructure were measured with dry mass of the porous nanostructure. If measured with a nanostructure sample suspended in an aqueous solution, the pore volume and the surface area are expected to be much higher than the measurements with the dry mass, as the density of the coating has been shown to be at least 10$^4$ lower than those reported in the art.

The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the porous nanostructure is fully extended in a buffer solution.

Example 4. Characterization of the Colored Nanostructures

Fluorescent magnetic nanoparticles with different fluorescent colors were prepared according to methods described in Examples 2 and 3. The magnetic nanoparticles and organic soluble semiconductor quantum dots were coated with the low density siliceous structure to make the water soluble biocompatible fluorescent magnetic nanoparticles. The fluorescence could also be added onto the particles by covalent linking of organic fluorophores after magnetic nanoparticles being coated with the low density siliceous coating.

Figure 7:
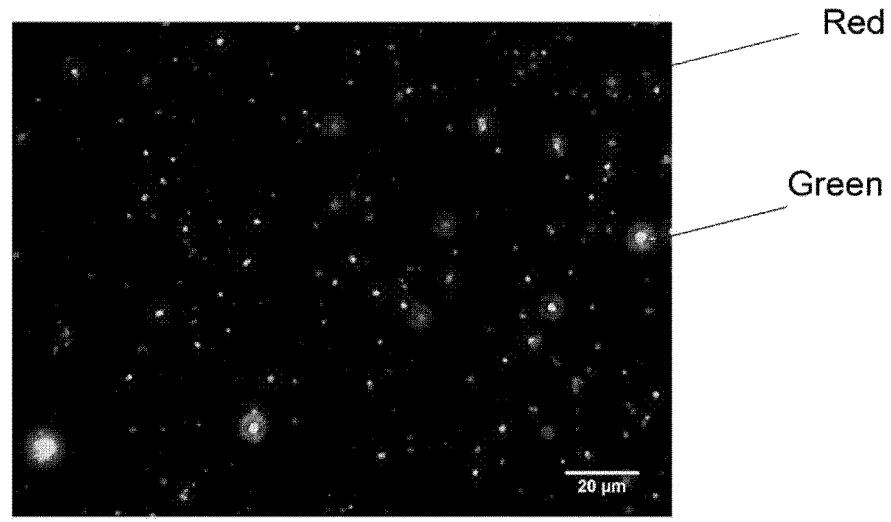
FIG. 7 shows fluorescent magnetic nanostructures with bright and stable fluorescence. Individual nanostructure fluorescence could be easily imaged using a common microscope. Multiple colors could be imaged using single wavelength excitation.

The nanoparticles with different colors were premixed together in solution, then a drop of solution was dropped onto a glass slide, and imaged with a fluorescent microscope using a single excitation filter in the blue color range, and the emission filter of a long path 525 nm filter. Image was taken using a color camera. Multiplexed fluorescent color could be captured simultaneously using the same color camera, as shown in FIG. 7.

Example 5. Characterization of the Fluorescent Nanostructures in Cell Culture

Figure 8:
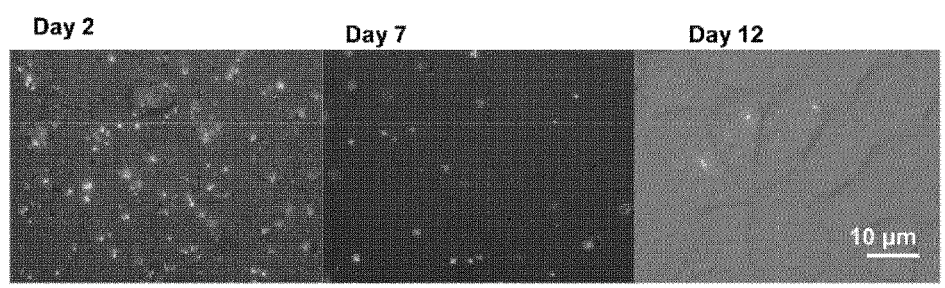
FIG. 8 shows that fluorescent magnetic nanostructures are very biocompatible. They are passed to daughter cells, and the fluorescence signal could be imaged for many days.

Fluorescent magnetic nanoparticles are mixed into cell culture media. Cells were then cultured following general cell culture protocol for 12 days until no nanoparticles were observed. Cells were imaged using a fluorescent microscope at different time points. Since such nanoparticles were biocompatible, they could be uptaken by cells, and passed to daughter cells. As cells split, number of nanoparticles per cell decreased (as shown in FIG. 8). The fluorescence signal from the particles was very stable, showing no fluorescence decrease after 12 days.

Example 6. Characterization of the Magnetic Property of the Nanostructures

Figure 9:
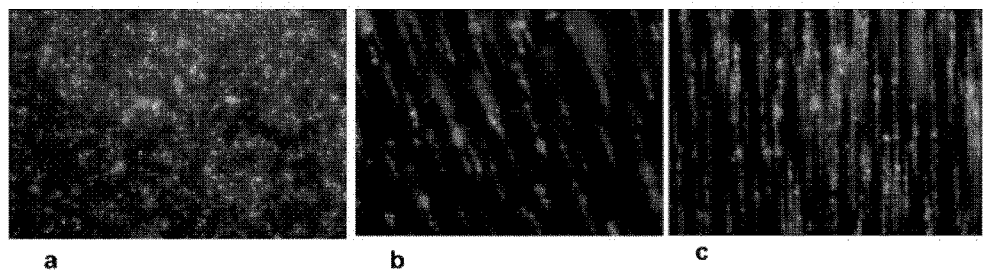
FIG. 9 shows that fluorescent magnetic nanostructures could easily respond to external magnetic field control. Fluorescent magnetic nanostructures dispersed in a random manner when there is no external magnetic field applied (a), but are aligned in response to an applied magnetic field (b and c).

Different fluorescent magnetic nanoparticles were mixed together in solution. A drop of the solution was applied on top of a glass slide. The fluorescent magnetic nanoparticles were randomly dispersed when there was no external magnetic field (FIG. 9a). When a small permanent magnet was rotating underneath the glass slide, the fluorescent magnetic nanoparticles responded to the external magnetic field and moved as the magnet underneath the glass slide moves (see FIGS. 9b and c). The images were taken using a fluorescent magnetic microscope with the same excitation filter of a blue color range and a long path emission filter of the green color range. Multiple fluorescent colors could be captured simultaneously using a color camera. These fluorescent magnetic nanoparticles also easily responded to external magnetic field gradient generated using common magnet, allowing magnetic manipulation or spreading onto a magnetic grid on a surface.

Example 7. Detection of Different Cells

Figure 13:
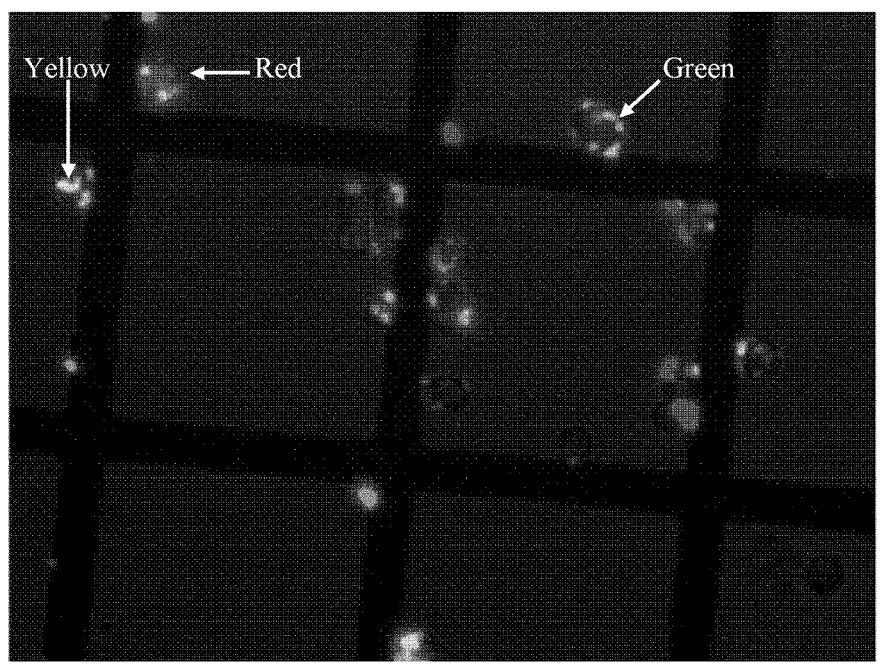
FIG. 13. Experimental data shows that fluorescent magnetic nanoparticles with different emission wavelength (green, yellow, red) are conjugated with anti-Her2, anti-EpCAM and anti-EGFR antibodies, they are used to identify different cells based on their surface marker difference. The labeled cells could be spread onto a magnetic mesh for capture and identification.

Fluorescent magnetic nanoparticles with different fluorescence color were conjugated with streptavidin first, then the antibodies were biotinylated and mixed with different emission colored beads. As shown in FIG. 13, fluorescent magnetic nanoparticles with different emission wavelength (green, yellow, red) were conjugated with anti-Her2, anti-EpCAM and anti-EGFR antibodies respectively, which were used to identify different cells based on their surface marker difference. After magnetic separation, the antibody conjugated beads were incubated with mixture of 3 types of cells of LnCAP, MCF-7, and PC3 for 2 hours. Afterwards, cell solution were run through the surface of the magnetic mesh, captured by the mesh and spread on the mesh surface for identification. As a result, the cells were labeled by the differently colored nanoparticles, and the identity of the cells was shown by the difference in color.

Example 8. Separation of a Desired Population of Cells

Figure 14:
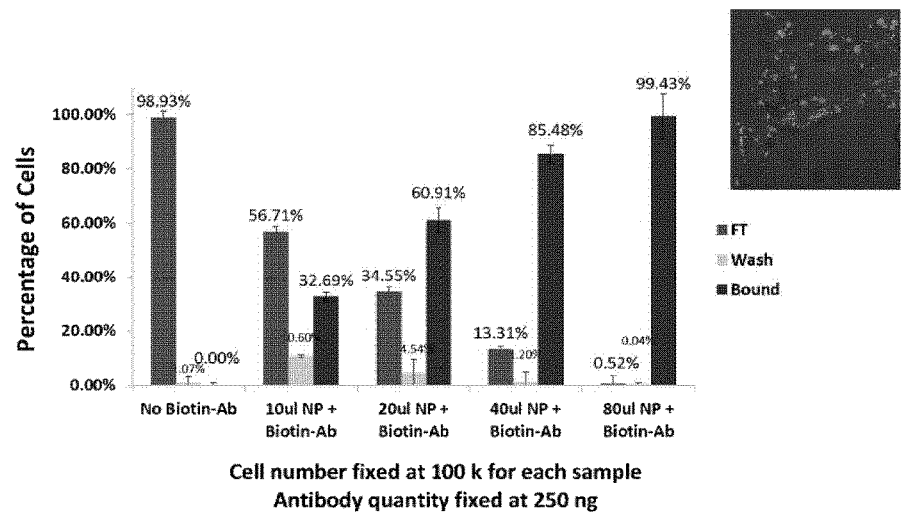
FIG. 14. Capture of target cells is enhanced with an increased amount of nanoparticles although the analyte binding member remains in constant amount. different percentage of cells by fixing cell number at 100 k and antibody quantity at 250 ng. It indicates that the percentage of bound cells increases with the number of magnetic nanoparticles. In another words, the magnetic nanoparticles can be used to select a desired population of cells by adjusting the ratio of the number of the magnetic beads to the cells. For example, this property could be used to select antibody high producer cells, or specific cells with a low thresh-hold of number of markers on surface.

Fluorescent magnetic nanoparticles were conjugated with streptavidin, and mixed with biotinylated antibody. A constant amount of 250 ng antibody was mixed with different amounts of the nanoparticles, i.e., at 10 ul, 20 ul, 40 ul, and 80 ul, to prepare four different test compositions. Then the four test compositions were added respectively to four samples, each with a fixed cell number of 100 000 cells expressing the antigen. The cells were incubated with the test compositions to allow capture of the cells by the antibody on the nanoparticles, and then were separated by flowing through a magnetic grid. The magnetic grid was washed with PBS, and then eluted with an eluting buffer. The solution obtained after flowthrough ("FT"), washing ("Wash") and eluting ("Bound") were collected respectively, and detected for the amount of cells (see FIG. 14). The percentage of captured cells increased with the increase in the amount of the magnetic nanoparticles, although the amount of the antibody remained the same. The percentage of the cells was up to 99.43% when 80 µl of magnetic nanoparticles was used, whereas when 10 µl of magnetic nanocomposition was added to the sample, the percentage of captured cells was 32.69%.

Figure 15:
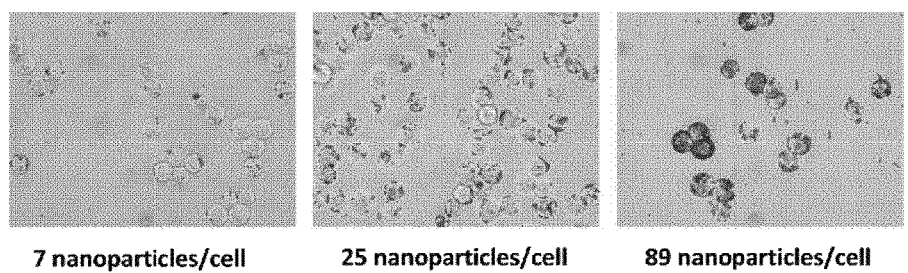
FIG. 15 shows bright field images of three samples with different number of nanoparticles per cell. It indicates that the number of nanoparticles per cell can be controlled by the starting ratio of the number of nanoparticles to the number of cells before incubation. These figures show the cells tagged with different average number of beads. These cells are magnetically captured to the side of a vial using a magnet, then re-dispersed in cell medium and imaged under microscope.

The number of nanoparticles per cell could be controlled by the starting ratio of the number of nanoparticles to cells before incubation. Cells were mixed with magnetic nanoparticles at different ratios, namely, 7 nanoparticles/cell, 25 nanoparticles/cell, and 89 nanoparticles/cell. These cells were magnetically captured to the side of a vial using a magnet, and then re-dispersed in cell medium and imaged under microscope. As shown in FIG. 15, by adjusting the starting ratio of the number of nanoparticles to cells, the bright field images showed the cells were tagged with different average number of beads. The cells of desired number of nanoparticle per cell are selected to represent a high presence or expression of the analyte.

Example 9. Purification and Labelling of Cells

Figure 16:
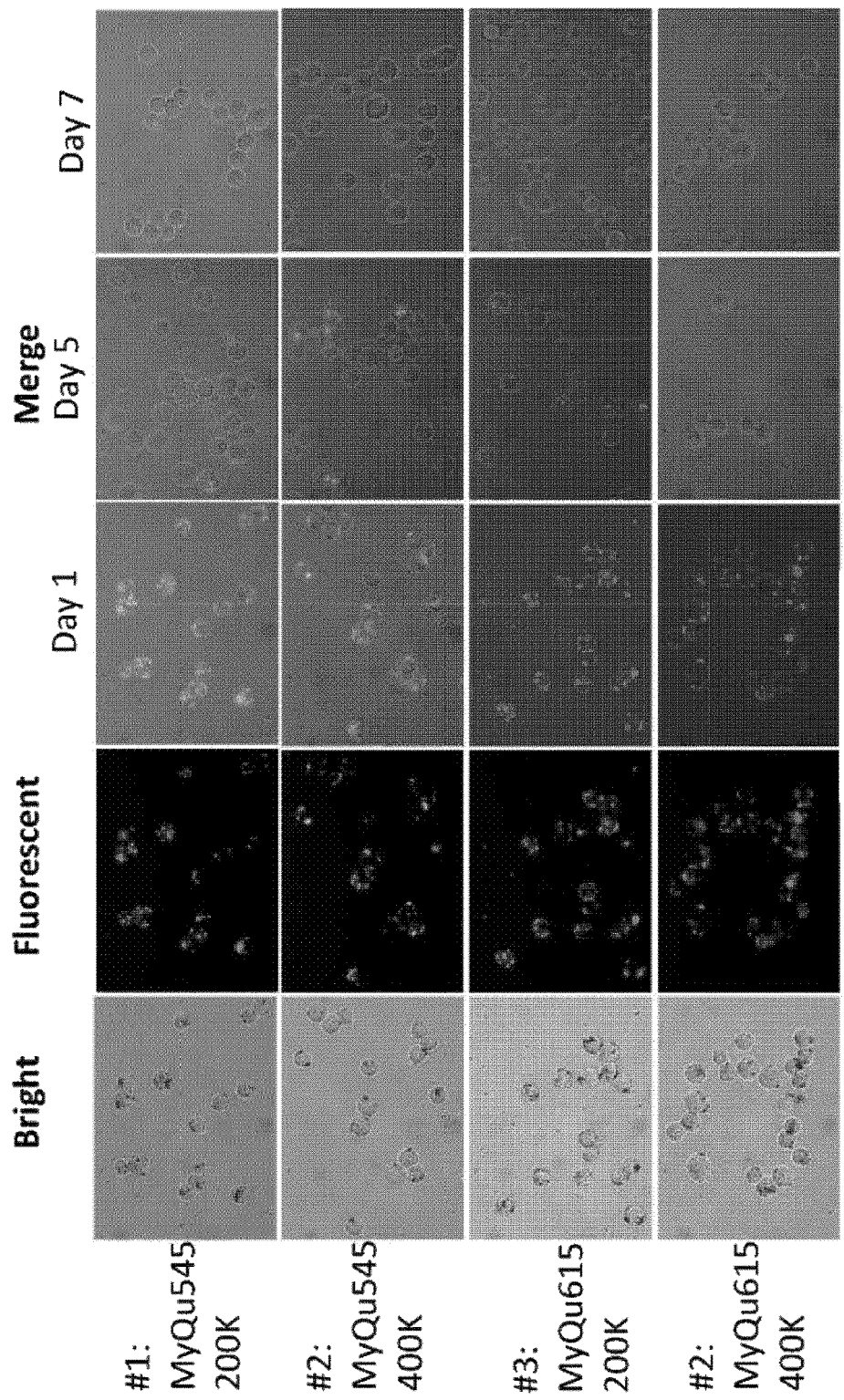
FIG. 16 shows fluorescent magnetic nanoparticles for high capacity cell purification and concurrent labeling. The nanoparticles are streptavidin coated, then conjugated with biotinlyated-EpCAM antibody. Cell lines used are human breast cancer cell MCF-7. Cells are tagged with nanoparticles, as cells divide, number of nanoparticle per cell decreases, after 5-7 days, majority of cells contain no nanoparticles.

Fluorescent magnetic nanoparticles were coated with streptavidin and then conjugated with biotinlyated-EpCAM antibody. Cell lines used here were human breast cancer cell MCF-7. As shown in FIG. 16, the cells were tagged with nanoparticles, as cells divided, the number of nanoparticles per cell decreased. After 5-7 days, majority of cells contained no nanoparticles.

Example 10. Recovery of Trace Amount of Cancer Cells

Figure 17:
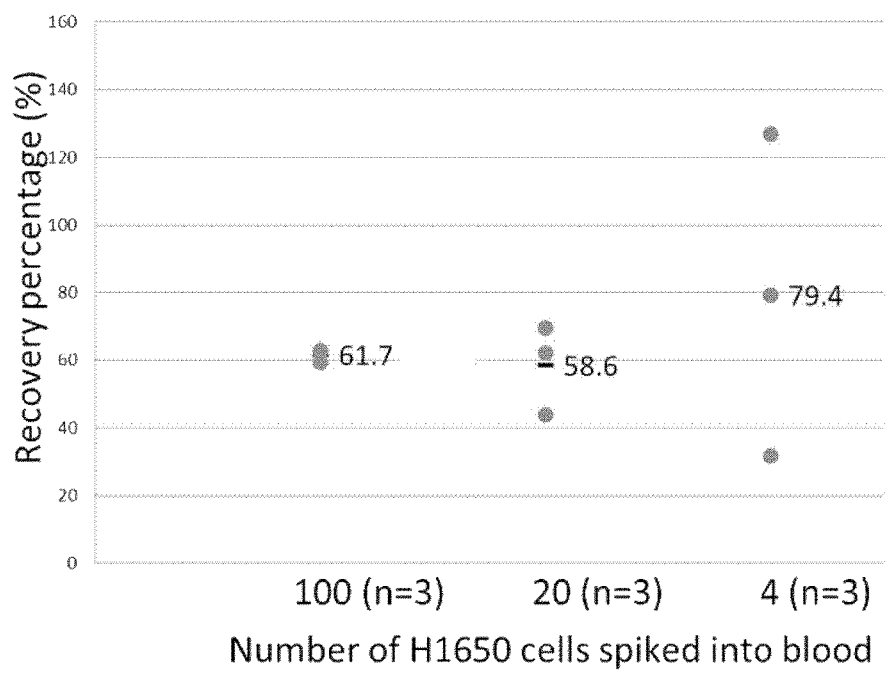
FIG. 17 shows magnetic nanoparticles can be used to capture and identify circulating tumor cells from whole blood samples. The recovery efficiency is high even for low number of cancer cells spiked into whole blood. The H1650 cells are used to evaluate the recovery efficiency herein.

Fluorescent magnetic nanoparticles were coated with streptavidin and then conjugated with biotinlyated-EpCAM antibody. 100, 20 or 4 H1650 cells prestained with CFSE of green fluorescence were spiked into 1 ml whole blood. The blood sample spiked with the H1650 cells were incubated with the magnetic nanoparticles, followed by magnetic pull down with a small magnet. After removing the supernatant, the cells were redispersed in medium and counted. As shown in FIG. 17, the recovery efficiency was high even for low number of spiked H1650 cells.

Figure 18:
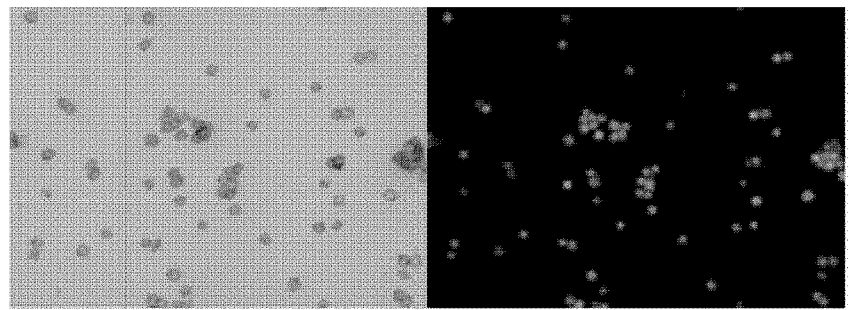
FIG. 18 shows purity of magnetically separated cancer cells from whole blood samples is almost 100%. The left figure shows the bright field image of magnetically separated 400 k H1650 cells from whole blood. The right figure shows the corresponding fluorescent cell image by pre-labeling these cells with CFSE staining.

In another experiment, 400,000 H1650 cells pre-labeled with CFSE staining were recovered from whole blood samples, using magnetic nanoparticles. As shown in FIG. 18, for each cell shown in the bright field image (left), there is a corresponding florescent cell image (right), indicating that the cells recovered from the whole blood are in high purity (almost 100%).

The invention claimed is:

1. A composition comprising
    (a) a nanostructure linked to a first analyte-binding member capable of binding to an analyte; and
    (b) a first signal indicator,
    wherein the nanostructure comprises a core nanoparticle coated with a porous 3-D structure having a density of <1.0 g/cc,
    wherein the first signal indicator contains a second analyte-binding member capable of binding to the analyte and a first detectable signal,
    wherein the porous 3-D structure is made of organosilane,
    wherein the core nanoparticle comprises a magnetic material, and
    wherein the density is determined using the dry mass of the 3-D structure divided by the total volume of the 3-D structure in an aqueous solution.

2. The composition of claim 1 wherein the nanostructure is colored or non-colored.

3. The composition of claim 2 wherein the colored nanostructure is bar-coded or associated with a detectable agent to show a color.

4. The composition of claim 3 wherein the detectable agent is a fluorescent molecule, a chemo-luminescent molecule, a bio-luminescent molecule, a radioisotope, a MRI contrast agent, a CT contrast agent, an enzyme-substrate label, or a coloring agent.

5. The composition of claim 1 wherein the magnetic material is a ferromagnetic material, a ferrimagnetic material, paramagnetic material, or a superparamagnetic material.

6. The composition of claim 1 wherein the first analyte-binding member is selected from the groups consisting of Protein A, Protein G, a protein/peptide, an antibody or fragments thereof, a nucleic acid, a first molecule capable of specifically binding to a second molecule, carbohydrate, lipid, a polymer, a small organic molecule, a ligand, a receptor, a guest chemical, and a host chemical.

7. The composition of claim 1 further comprising the analyte, wherein the first analyte-binding member and the second analyte-binding member specifically bind to the analyte.

8. The composition of claim 7 wherein the analyte is selected from the group consisting of a biological sample, a cell, a virus, an antibody, a protein/peptide, a nucleic acid, carbohydrate, lipid, a polymer, a small organic molecule, a ligand, a receptor, a guest molecule, and a host molecule.

9. The composition of claim 1 wherein the first detectable signal is a first detectable agent or a non-magnetic colored nanostructure.

10. The composition of claim 1 wherein the second analyte-binding member is selected from a group consisting of Protein A, Protein G, a protein/peptide, an antibody or fragments thereof, a nucleic acid, a first molecule capable of specifically binding to a second molecule, carbohydrate, lipid, a polymer, a small organic molecule, a ligand, a receptor, a guest chemical, and a host chemical.

11. The composition of claim 1 wherein the first analyte-binding member is capable of binding to a first region of the analyte and the second analyte-binding member is capable of binding to a second region of the analyte, wherein the first region of the analyte does not overlap with the second region of the analyte.

12. The composition of claim 11 further comprising a second signal indicator wherein the second signal indicator contains a third analyte-binding member capable of binding to the analyte and a second detectable signal.

13. The composition of claim 12 wherein the third analyte-binding member is capable of binding to a third region of the analyte that do not overlap with the first region of the analyte or the second region of the analyte.

14. The composition of 12 wherein the second detectable signal is the same as the first detectable signal.

15. The composition of claim 1 further comprising a substrate having a magnetic grid wherein the magnetic nanostructure is dispersed onto the magnetic grid.

16. A multiplex system comprising a first magnetic nanostructure having a first analyte-binding member capable of binding to a first analyte and a second magnetic nanostructure having a second analyte-binding member capable of binding to a second analyte, wherein each of the magnetic nanostructure comprises at least one core nanoparticle coated with a porous 3-D structure having a density of <1.0 g/cc, wherein the porous 3-D structure is made of organosilane, and wherein the density is determined using the dry mass of the 3-D structure divided by the total volume of the 3-D structure in an aqueous solution.

17. The multiplex system of claim 16 further comprising a first signal indicator and a second signal indicator; wherein the first signal indicator comprises a first signal-indicator analyte binding member capable of binding to the first analyte and a first detectable signal and the second signal indicator comprises a second signal-indicator analyte binding member capable of binding to the second analyte and a second detectable signal.

18. The multiplex system of claim 16 further comprising a substrate having a magnetic grid, wherein the first and the second magnetic nanostructures can be dispersed onto the magnetic grid.

19. A method of determining the presence and/or quantity of an analyte in a sample comprising the steps of:
   a) contacting the sample with the composition of claim 3 in a mixture; and
   b) detecting and quantifying the co-location of the color of the colored magnetic nanostructure and the analyte.

20. The method of claim 19 wherein the co-location is determined by either dispersing the mixture onto a substrate having a magnetic grid and observing under optical lens or by passing light through the mixture in solution from a microlens array to a photosensor array and analyzing light data.

21. A method of determining the presence and/or quantity of an analyte in a sample comprising the steps of:
   a) contacting the sample with the composition of claim 1 to form a mixture;
   b) dispersing the mixture onto a magnetic grid; and
   c) detecting and quantifying the detectable signal of the signal indicator.

22. A method of determining the presence and/or quantity of an analyte in a sample comprising the steps of:
   a) contacting the sample with the composition of claim 15;
   b) measuring the presence and/or quantity of an analyte.

23. A method of determining the presence and/or quantity of a first analyte and a second analyte in a sample comprising the steps of:
   a) contacting the sample with the multiplex system of claim 18; and
   b) measuring the presence and/quantity of the analytes.

24. The method of claim 19, further comprising separating the analyte from the sample.

25. The method of claim 19, wherein the analyte is selected from the group consisting of a biological sample, a cell, a virus, an antibody, a protein/peptide, a nucleic acid, carbohydrate, lipid, a polymer, a small organic molecule, a ligand, a receptor, a guest molecule, and a host molecule.

26. The method of claim 25, wherein the cell is an antibody-producing hybridoma cell, a circulating tumor cell or a cell expressing a disease marker.

27. A method of determining the presence and/or quantity of an analyte in a sample comprising the steps of:
   a) contacting the sample with the composition of claim 2, 3 or 4 to form a mixture;
   b) loading the mixture to a loading region of a lateral flow test strip, wherein the test strip comprises a detection region comprising an immobilized second analyte-binding member; and
   c) detecting and/or quantifying the analyte at the detection region of the test strip.

28. The method of claim 27, further comprising applying a magnetic field to the test strip to remove the composition of claim 2, 3 or 4 that is unbound to the second analyte-binding member.

29. A method of determining the presence and/or quantity of a first analyte and a second analyte in a sample comprising the steps of:
   a) contacting the sample with the multiplex system of claim 16 to form a mixture;
   b) dispersing the mixture onto a magnet grid; and
   c) measuring the presence and/quantity of the analytes.

* * * * *